(12) United States Patent
Webler et al.

(10) Patent No.: US 7,828,819 B2
(45) Date of Patent: Nov. 9, 2010

(54) CORD LOCKING MECHANISM FOR USE IN SMALL SYSTEMS

(75) Inventors: William E. Webler, Escondido, CA (US); Dwight A. Ambat, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1309 days.

(21) Appl. No.: 10/740,360

(22) Filed: Dec. 17, 2003

(65) Prior Publication Data

US 2004/0133274 A1    Jul. 8, 2004

Related U.S. Application Data

(63) Continuation-in-part of application No. 10/295,714, filed on Nov. 15, 2002, now Pat. No. 7,485,143.

(51) Int. Cl.
*A61L 17/00* (2006.01)
(52) U.S. Cl. ..................... 606/232; 24/115 R
(58) Field of Classification Search ......... 254/398–417; 403/374.2, 211; 606/153, 108, 113, 120, 606/203, 232; 24/115, 115 R
See application file for complete search history.

(56) References Cited

U.S. PATENT DOCUMENTS

| | | | |
|---|---|---|---|
| 3,177,543 A * | 4/1965 | Fountain | 188/65.2 |
| 3,716,058 A | 2/1973 | Tanner, Jr. | |
| 4,128,100 A | 12/1978 | Wendorff | |
| 4,719,924 A | 1/1988 | Crittenden et al. | |
| 4,781,186 A | 11/1988 | Simpson et al. | |
| 4,817,250 A * | 4/1989 | Kurosaki | 24/115 G |
| 4,830,023 A | 5/1989 | de Toledo et al. | |

(Continued)

FOREIGN PATENT DOCUMENTS

DE   10161543   6/2003

(Continued)

OTHER PUBLICATIONS

Robert O. Bonow, et al., "Guidelines for the Management of Patients with Valvular Health Disease," Report of American College of Cardiology/American Heart Assoc. Task Force on Practice Guidelines (Committee on Management of Patients with Valvular Heart Disease), American College of Cardiology and American Heart Assoc., Inc., 1998, pp. 1949-1984.

(Continued)

*Primary Examiner*—Todd E Manahan
*Assistant Examiner*—Michael G Mendoza
(74) *Attorney, Agent, or Firm*—Jonathan D. Feuchtwang; Blakely Sokoloff Taylor & Zafman LLP

(57) ABSTRACT

A locking device that can be used to adjust a cord of a small system or a medical device. The locking device includes an outer housing having a first lumen. A cord is disposed within the first lumen where the cord is freely moveable through the first lumen. A locking mechanism is disposed within the first lumen and over the cord. The locking mechanism is configured to lock or unlock the cord relative to the outer housing. An actuator is configured to move the locking mechanism to lock or unlock the cord relative to the outer housing.

38 Claims, 12 Drawing Sheets

U.S. PATENT DOCUMENTS

| | | |
|---|---|---|
| 4,920,980 A | 5/1990 | Jackowski |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,171,233 A | 12/1992 | Amplatz et al. |
| 5,201,598 A * | 4/1993 | Tehan ..................... 403/372 |
| 5,234,443 A | 8/1993 | Phan et al. |
| 5,242,456 A | 9/1993 | Nash et al. |
| 5,350,395 A | 9/1994 | Yock |
| 5,358,479 A | 10/1994 | Wilson |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,487,757 A | 1/1996 | Truckai et al. |
| 5,495,974 A | 3/1996 | Deschenes et al. |
| 5,518,162 A | 5/1996 | Deschenes et al. |
| 5,522,873 A | 6/1996 | Jackman et al. |
| 5,531,686 A | 7/1996 | Lundquist et al. |
| 5,554,184 A | 9/1996 | Machiraju |
| 5,569,277 A | 10/1996 | Evans et al. |
| 5,571,215 A | 11/1996 | Sterman et al. |
| 5,588,188 A * | 12/1996 | Jermyn, Jr. ................. 24/598.7 |
| 5,609,598 A | 3/1997 | Laufer et al. |
| 5,613,937 A | 3/1997 | Garrison et al. |
| 5,617,854 A | 4/1997 | Munsif |
| 5,632,754 A | 5/1997 | Farley et al. |
| 5,640,955 A | 6/1997 | Ockuly et al. |
| 5,642,736 A | 7/1997 | Avitall |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,728,129 A | 3/1998 | Summers |
| 5,782,828 A | 7/1998 | Chen et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,123,699 A | 9/2000 | Webster, Jr. |
| 6,149,669 A | 11/2000 | Li |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,178,346 B1 | 1/2001 | Amundson et al. |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,203,531 B1 | 3/2001 | Ockuly et al. |
| 6,210,407 B1 | 4/2001 | Webster, Jr. |
| 6,210,432 B1 | 4/2001 | Solem et al. |
| 6,231,587 B1 | 5/2001 | Makower |
| 6,241,728 B1 | 6/2001 | Gaiser et al. |
| 6,254,568 B1 | 7/2001 | Ponzi |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,355,030 B1 | 3/2002 | Aldrich et al. |
| 6,371,978 B1 | 4/2002 | Wilson |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,537,198 B1 | 3/2003 | Vidlund et al. |
| 6,537,314 B2 | 3/2003 | Langberg et al. |
| 6,551,271 B2 | 4/2003 | Nguyen |
| 6,554,794 B1 | 4/2003 | Mueller et al. |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,638,286 B1 | 10/2003 | Burbank et al. |
| 6,638,289 B1 | 10/2003 | Johnson et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,065 B2 | 3/2004 | Langberg |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,733,500 B2 | 5/2004 | Kelley et al. |
| 6,755,812 B2 | 6/2004 | Peterson et al. |
| 6,761,734 B2 | 7/2004 | Suhr |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg |
| 6,824,562 B2 | 11/2004 | Mathis et al. |

| | | | |
|---|---|---|---|
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 7,073,504 B2 | 7/2006 | Callister et al. |
| 7,160,318 B2 | 1/2007 | Greenberg et al. |
| 7,186,264 B2 | 3/2007 | Liddicoat et al. |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis et al. |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059351 A1 | 3/2004 | Eigler et al. |
| 2004/0098092 A1 | 5/2004 | Butaric et al. |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2005/0045183 A1 | 3/2005 | Callister et al. |
| 2005/0055089 A1 | 3/2005 | Macoviak et al. |
| 2005/0085844 A1 | 4/2005 | Tremulis et al. |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |

FOREIGN PATENT DOCUMENTS

| | | |
|---|---|---|
| EP | 0377269 A1 | 7/1990 |
| WO | WO 98/29041 A1 | 7/1998 |
| WO | WO 99/00059 | 1/1999 |
| WO | WO 99/13777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06028 A1 | 2/2000 |
| WO | WO 00/66027 A2 | 2/2000 |
| WO | WO 00/16700 A1 | 3/2000 |
| WO | WO 00/60995 | 10/2000 |
| WO | WO 00/66027 A2 | 11/2000 |
| WO | WO 01/00111 A1 | 1/2001 |
| WO | WO 01/00114 A1 | 1/2001 |
| WO | WO 01/26557 A1 | 4/2001 |
| WO | WO 01/28432 A1 | 4/2001 |
| WO | WO 01/28455 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062263 A3 | 8/2002 |
| WO | WO 02/062270 A1 | 8/2002 |
| WO | WO 02/062408 A2 | 8/2002 |
| WO | WO 02/063533 | 8/2002 |
| WO | WO 02/078576 | 10/2002 |
| WO | WO 03/049619 A2 | 6/2003 |
| WO | WO 03/073913 A2 | 9/2003 |
| WO | WO 2004/012789 A2 | 2/2004 |
| WO | WO 2004/014282 A2 | 2/2004 |
| WO | WO-2004045463 | 6/2004 |

OTHER PUBLICATIONS

Messas, et al., "Chordal Cutting a New Therapeutic Approach for Ischmic Mitral Regurgitation," 2001, American Heart Association Inc., pp. 1958-1963.

PCT Search Report, Application No. PCT/US03/36633, Filed Nov. 13, 2003, mailed Aug. 9, 2004.

Abbott Cardiovascular Systems, PCT Search Report and Written Opinion dated Nov. 16, 2007 for PCT/US2007/011948.

Abbott Cardiovascular Systems, Non-Final Office Action mailed May 20, 2010 for U.S. Appl. No. 11/445,694.

Robert O. Bonow, et al., "Guidelines for the Management of Patients with Valvular Heath Disease," Report of American College of Cardiology / American Heart Assoc. Task Force on Practice Guidelines (Committee on Management of Patients with Valvular Heart Disease), American College of Cardiology and American Heart Assoc., Inc., 1998, pp. 1949-1984.

* cited by examiner

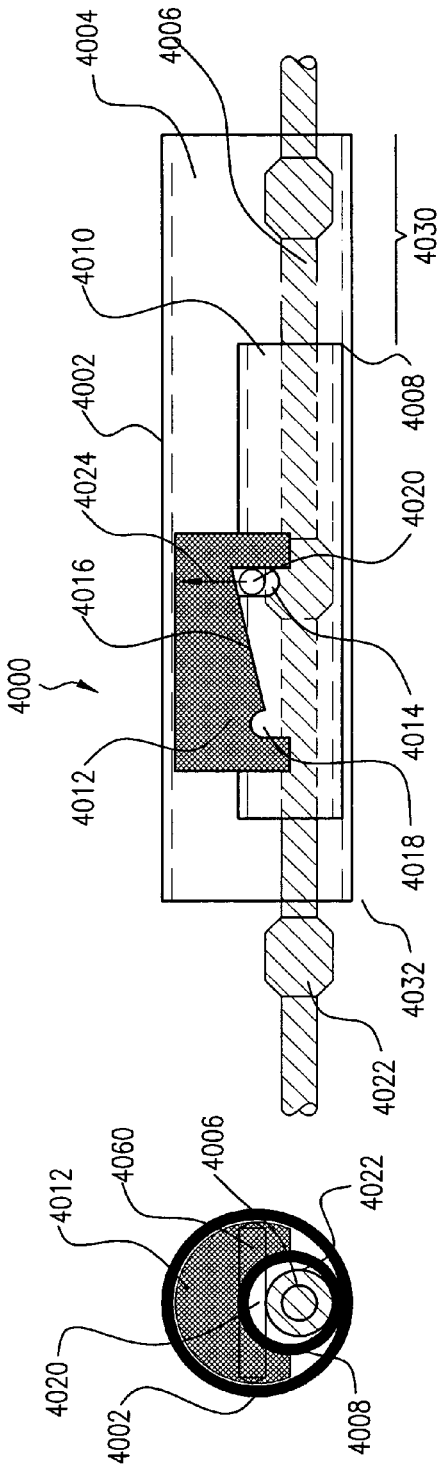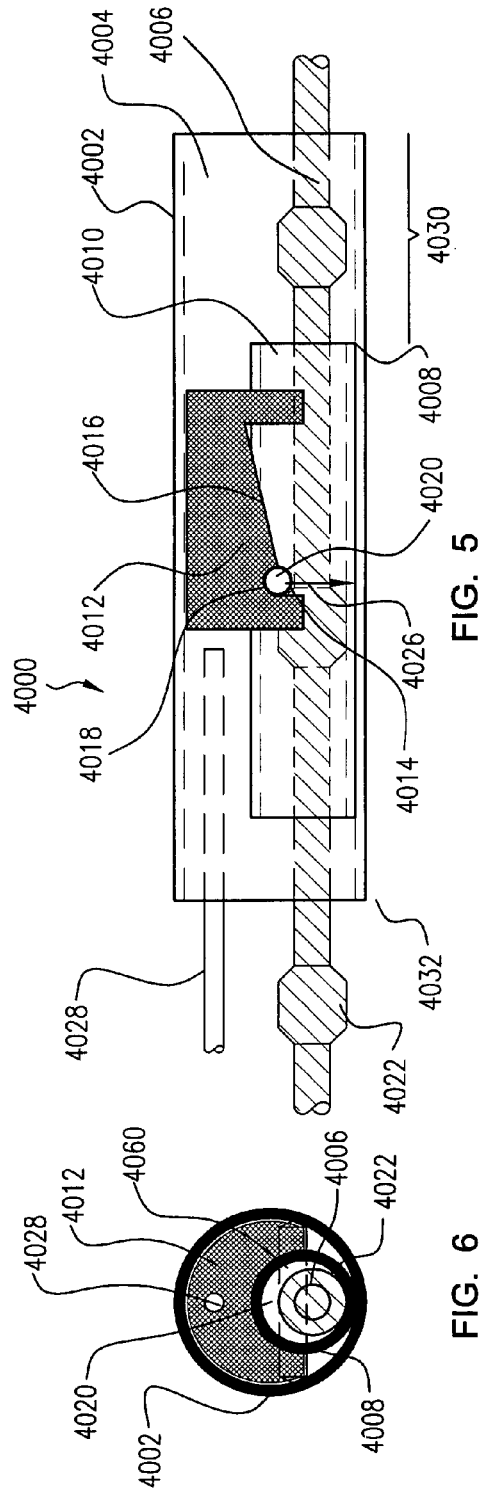

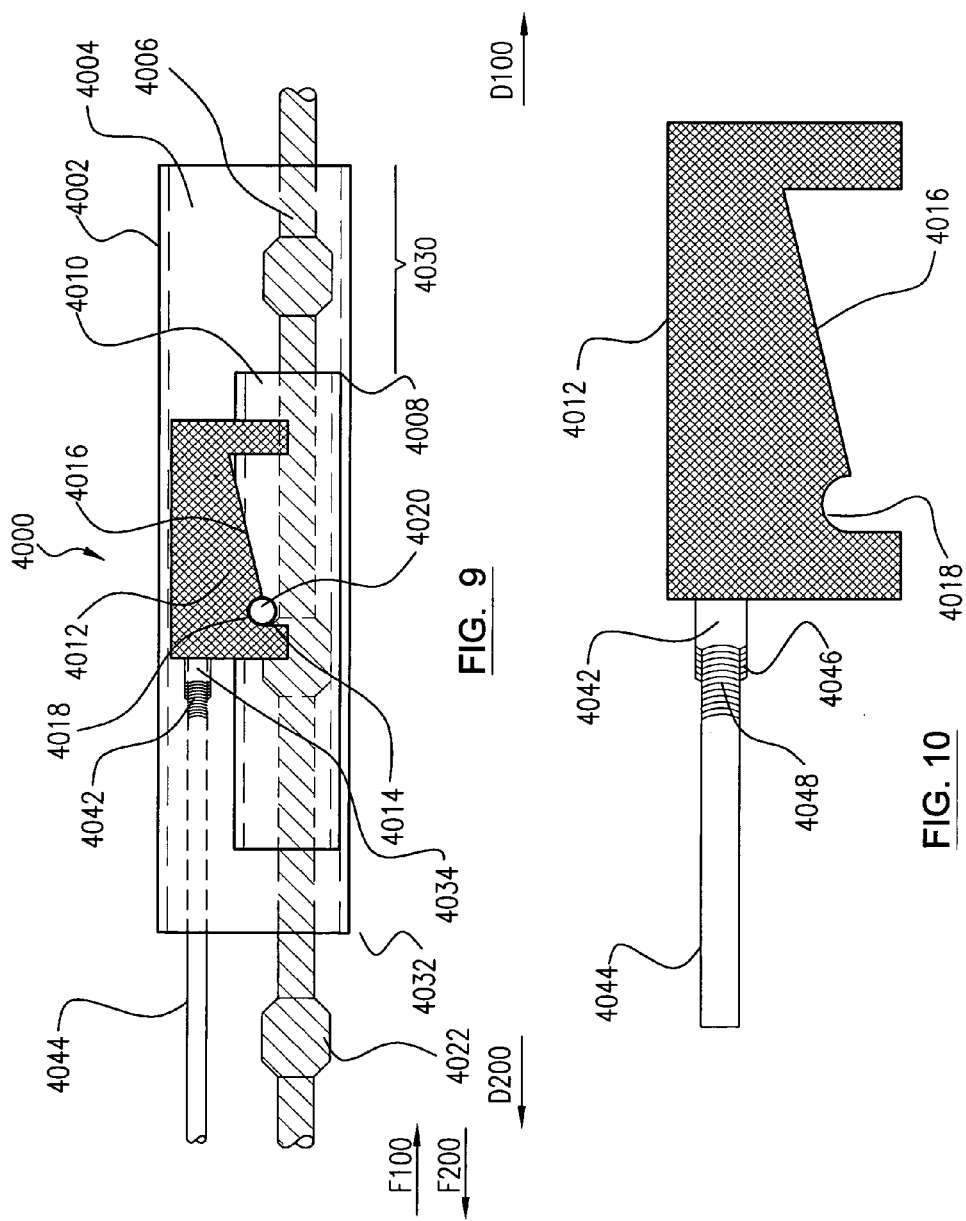

CORD LOCKING MECHANISM FOR USE IN SMALL SYSTEMS

RELATED APPLICATION

This is a continuation in part of U.S. patent application Ser. No. 10/295,714, filed on Nov. 15, 2002 now U.S. Pat. No. 7,485,143 entitled "Apparatuses and Methods for Heart Valve Repair". The mentioned Application is hereby incorporated by reference in its entirety.

BACKGROUND

1. Field

The present invention pertains to a cord locking mechanism for use in small systems, especially medical devices, such as heart valve repair apparatuses, implantable devices, devices with length adjustable devices, devices with telescoping sections, grasping devices, devices with deflecting sections or other devices that can be actuated by a cord. Additionally, the cord locking mechanism may be used to release or retrieve a device.

2. Discussion of Related Art

There are many devices and medical devices that are actuated, adjusted, lengthened, or shorten by actions of a cord, filament, wire or other elongated member (these will be referred to as a cord in subsequent descriptions) included within the devices. For instance, some medical devices include a telescoping device to provide flexibility in length for the medical devices. These medical devices typically include cords/wires used to adjust the length of the telescoping device. In other examples, many medical devices employ a locking mechanism that locks a cord/wire included therein to maintain the shapes and/or position of the medical devices or to restrain the devices in a particular position such as those described in U.S. Pat. No. 4,128,100 and U.S. Pat. No. 6,402,781. Further, medical devices such as a deflectable catheter may also use a cord which is locked into position to maintain the shape of the deflectable portion of the deflectable catheter.

Locking devices for cords are generally large, complicated and difficult to operate, especially for percutaneous medical applications. The smallest and simplest available cord locking device mechanisms are demonstrated by the configurations found on common cable ties, but these designs do not allow the cord to move freely in both directions until locking is desired. Without the ability to move freely until locking is desired, an inadvertent and/or transitory over-adjustment cannot be reversed. In addition, these locking mechanisms cannot be easily unlocked. Such over-adjustments can be injurious and/or render the medical device ineffective or less effective than an optimum adjustment, so these available designs are often not safe or practical in most medical applications. A number of other locking devices involve a biasing spring and other more complex features and mechanisms to lock the cord in position. The more elements required in the design of cord locking devices, the greater the risk of failure of, the larger the size of, and the more expensive the locking devices.

SUMMARY

Some aspects of the invention embodiments pertain to a locking device that can be used to adjust a cord of a small system or a medical device. The locking device includes an outer housing having a first lumen. A cord is disposed within the first lumen where the cord is freely moveable through the first lumen. A locking mechanism is disposed within the first lumen and over the cord. The locking mechanism is configured to lock or unlock the cord relative to the outer housing. In some embodiments, to lock refers to as to bind, grip, clasp, create a friction hold, or to pinch the cord relative to the outer housing. An actuator is configured to move the locking mechanism to lock or unlock the cord relative to the outer housing.

In other aspects, the locking mechanism includes an inner housing having a second lumen. The cord is disposed within the second lumen. The inner housing has an opening cutting through a lateral axis of the inner housing such that the opening exposes a portion of the cord. A locking member is disposed on the outer surface of the inner housing. The locking member is configured to interact with a locking pin to lock or unlock the cord through the opening.

In other aspects, the invention embodiments pertain to a medical device that includes a locking device and an implantable device that can be modulated by a cord. The implantable device can be an annuloplasty device as previously described in U.S. application Ser. No. 10/297,714. The implantable device can also be another medical device that has one or more sections actuated by a cord. In one embodiment, the implantable device is coupled to the locking device at one end. In another embodiment, the locking device is configured to be an integral part of the implantable device. The cord is disposed within the implantable device and extended through the locking device. In one embodiment, the distal end of the cord is attached to the implantable device in order move, modulate, and lock the implantable device in place.

In yet other aspects, the locking device of the exemplary embodiments of the present invention is attached or made an integral part of any of the medical devices described in Ser. No. 10/297,714, which is hereby incorporated by reference in its entirety.

Another aspect of the invention embodiments pertains to a medical device that incorporates a locking device. The medical device includes a member actuated by a cord and the member is implantable within a patient. The medical device also includes a locking device configured to lock and/or unlock the cord. The locking device has an outer housing and a first lumen. The cord is disposed within the first lumen and is freely moveable through the first lumen. The locking device further has a locking mechanism disposed within the first lumen and over the cord. The locking mechanism is configured to lock or unlock the cord relative to the outer housing. An actuator is used move the locking mechanism in order to lock and/or unlock the cord relative to the locking device.

Another aspect of the invention embodiments pertains to the use of the described mechanisms as an unlocking device to release devices from a delivery system, such as a percutaneous catheter delivery system. In one embodiment, the unlocking device is a part of the delivery system and the cord is a part of the device to be released. In another embodiment, the cord is a part of the delivery system and the unlocking device is a part of the device to be released.

Another aspect of the invention embodiments pertains to the use of the locking mechanisms to retrieve another device (e.g., an implantable device). In one embodiment, the device to be retrieved is configured to have a relatively stiff cord. A retrieval device configured to incorporate the locking device is provided. The locking device includes a guiding section (e.g., a funnel-like portion) to guide the cord into the locking device. The locking device can be actuated to constrain the relatively stiff cord and guide the cord into the locking device. The locking device is used to lock the relatively stiff cord in position. Once the cord is locked, the device to be retrieved can be withdrawn with the locking device.

BRIEF DESCRIPTION OF THE DRAWINGS

The present invention is illustrated by way of example and not limitation in the figures of the accompanying drawings, in which like references indicate similar elements and in which:

FIG. 3 illustrates a side view of an exemplary embodiment of a cord locking device in an unlocked condition;

FIG. 4 illustrates a cross-sectional view of an exemplary embodiment of a cord locking device in an unlocked condition;

FIG. 5 illustrates a side view of an exemplary embodiment of a cord locking device in a locked condition;

FIG. 6 illustrates a cross-sectional view of an exemplary embodiment of a cord locking device in a locked condition;

FIGS. 9-10 illustrates another exemplary embodiment of an engagement member included within a locking device;

DETAILED DESCRIPTION

Figure 1A:
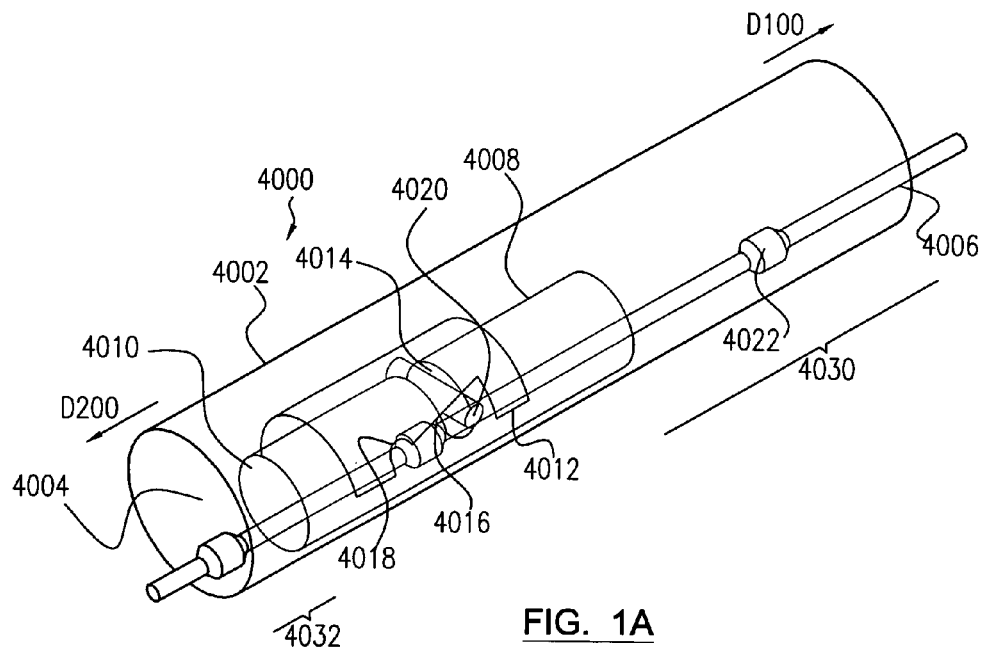
FIG. 1A illustrates a three-dimensional view of an exemplary embodiment of a cord locking device in an unlocked condition.

The exemplary embodiments of the present invention pertain to a cord locking mechanism for use in small systems such as heart valve repair apparatuses, implantable devices, catheters, percutaneous medical devices, medical devices with length adjustable devices, medical devices with telescoping devices, or other medical devices that can be actuated and/or adjusted by a cord.

In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

Aspects of the embodiments of the present invention pertain to a locking device that allows for a cord to be moved freely through the locking device and/or be locked into position and/or released from a locked condition. The locking device includes an outer housing having a lumen running longitudinally therethrough. A cord is disposed within the lumen. The cord is freely moveable through the lumen unless the lock is in a locked condition. A locking mechanism is disposed within the lumen and over the cord. A portion of the locking mechanism is configured to be able to move toward the cord and place the cord in a locked condition. An actuator is coupled to the locking mechanism to lock and/or unlock the cord relative to the outer housing. In some embodiments, to lock refers to as to bind, grip, clasp, create a friction hold, or to pinch the cord relative to the outer housing.

In other aspects, the locking mechanism includes an inner housing having a lumen running longitudinally therethrough. The inner housing is disposed within the outer housing such that the cord is disposed within the lumen of the inner housing. The inner housing is constrained or coupled to the outer housing. The inner housing includes an opening laterally cutting through a portion of the inner housing. A locking member is disposed on the outer surface of the inner housing and configured to interact with a locking pin to lock or unlock the cord through the opening.

The locking device can lock the cord, permanently or not permanently, in a longitudinally constrained position relative to the inner and outer housings. The locking device can be coupled with a medical device or a small system that can accommodate a cord such that the cord allows for a particular adjustment of the medical device or other small system. Examples of such a device include heart valve repair apparatuses, annuloplasty devices, implantable devices, medical devices with length adjustable devices, medical devices with telescoping devices, medical devices with deflecting sections, devices with grasping mechanisms or other devices that can be actuated and/or adjusted by a cord where a small device size is desired. As the locking device locks or unlocks the cord, the cord can be positioned to actuate and/or adjust the medical device or other small system as necessary. In one embodiment, the distal end of the cord is attached to the implantable device or at least a portion of the implantable device in order move, modulate, and lock the implantable device in place.

The locking device can be configured to be an unlocking device. In this configuration it may be used to release a device, such as an implanted device, from a delivery system, such as a catheter delivery system. In one embodiment, the unlocking device is a part of the delivery system and the cord is a part of the device to be released. In another embodiment, the cord is a part of the delivery system and the unlocking device a part of the device to be released.

FIGS. 1-6 illustrate an exemplary embodiment of a locking device 4000. The locking device 4000 is a miniature mechanism that allows a cord 4006 to be moved freely through the locking device 4000. In one embodiment, the locking device 4000 is configured to lock the position of the cord 4006 relative to the device 4000 with an actuator (e.g., a small pin or wire) 4028. The locking device 4000 can also be configured to unlock the position of the cord 4006. The locking device 4000 can be coupled to another device or a medical device that requires an adjustment using a cord and/or a device that is actuated by a cord. The locking device 4000 can also be made to be an integral part of the device or the medical device that requires an adjustment using a cord and/or actuation using a cord. The locking device 4000 can also be made to be an integral part of a delivery system used to deliver the medical device that uses a cord for adjustment or actuation.

Figure 1B:
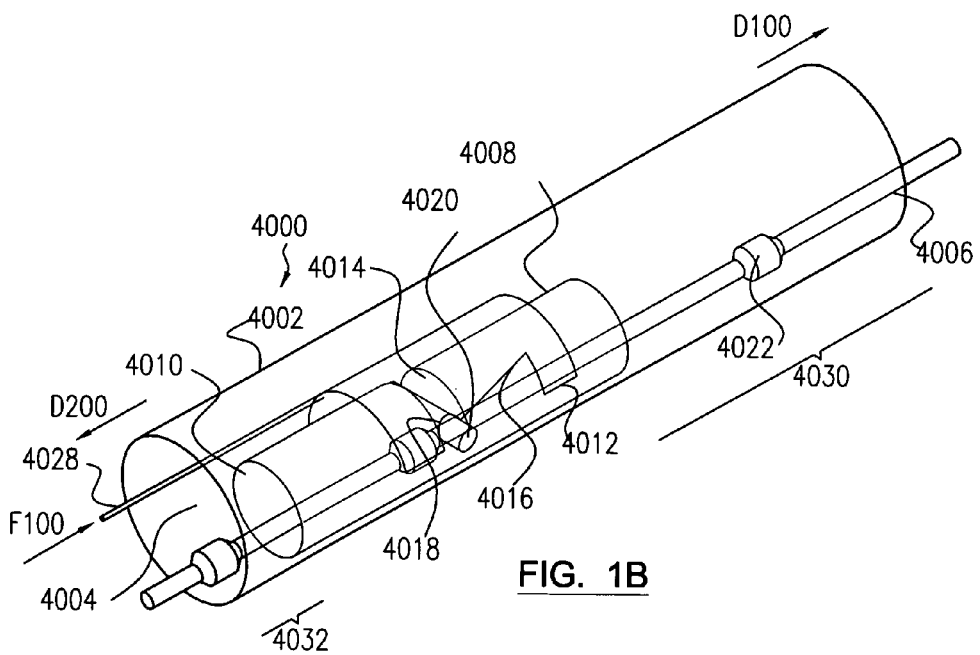
FIG. 1B illustrates a three-dimensional view of an exemplary embodiment of a cord locking device in a locked condition.
Figure 2A:
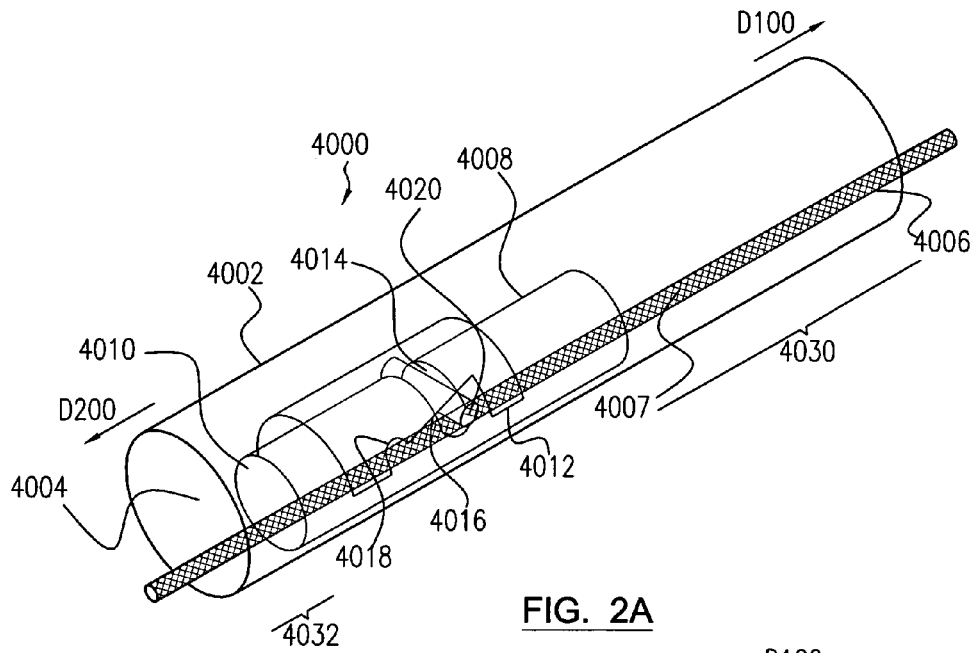
FIG. 2A illustrates a three-dimensional view of another exemplary embodiment of a cord locking device in an unlocked condition.
Figure 2B:
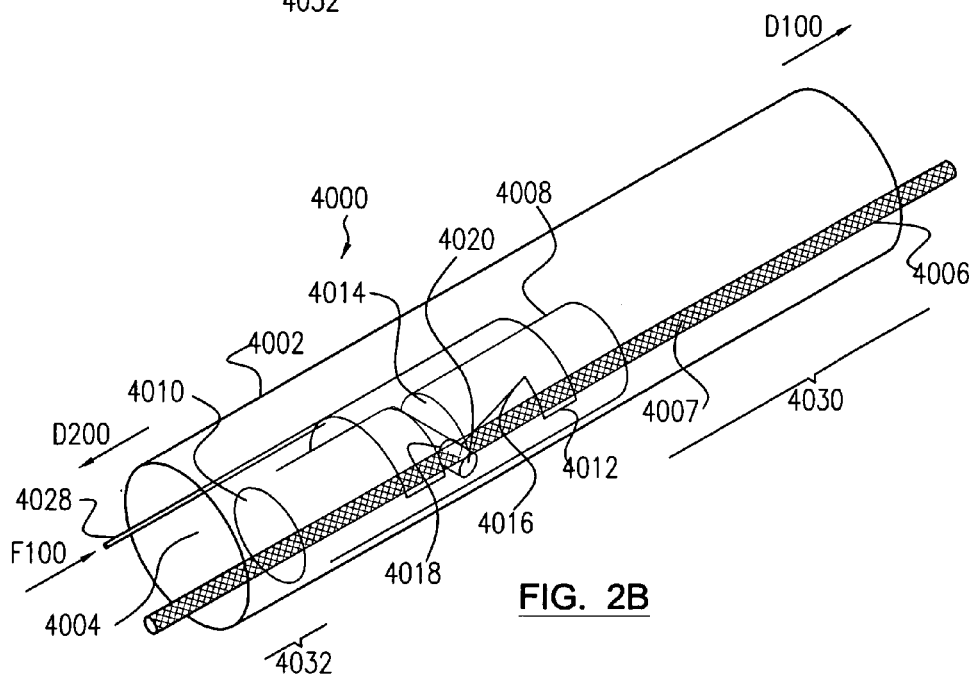
FIG. 2B illustrates a three-dimensional view of another exemplary embodiment of a cord locking device in a locked condition.

FIGS. 1A-1B are three-dimensional partial see-through views of the locking device 4000 with the cord 4006 in an unlocked condition (FIG. 1A) and the cord 4006 in a locked condition (FIG. 1B). FIGS. 2A-2B are three-dimensional partial see-through views of an alternative embodiment of the locking device 4000 with the cord 4006 in an unlocked condition (FIG. 2A) and the cord 4006 in a locked condition (FIG. 2B). FIGS. 3 and 5 are partial see-through views of the locking device 4000 shown in the unlocked and then in the locked conditions, respectively. FIGS. 4 and 6 are proximal end cross-sectional views of the locking device 4000 in the unlocked and then in the locked conditions, respectively.

In some embodiments, the outer housing 4002 and inner housing 4008 have tubular shape as shown in FIGS. 1A-1B. The tubular shape makes the design, construction and manufacturing of the outer housing 4002, the locking member 4012 and the inner housing 4008 easier and more compatible with catheter and cord constructions. In other embodiments, the outer housing 4002 and the inner housing 4008 may have other configurations such as with square, oval, hexagonal, etc.

In one embodiment, the locking device 4000 includes an outer housing 4002, an inner housing 4008, a cord 4006, a locking member 4012, and a locking pin 4020 (FIGS. 1A-1B or FIGS. 3-6). In one embodiment, the inner housing 4008, the locking member 4012, and the locking pin 4020 form the locking mechanism of the locking device 4000. The locking mechanism is configured so that it can lock the cord 4006 in position relative to the locking device 4000. The locking mechanism is also configured so that it can unlock the cord 4006 from a locked condition.

In one embodiment and as shown in FIGS. 1A-1B, 3, and 5, the outer housing 4002 has a lumen 4004 running longitudinally therethrough. The cord 4006 is disposed within the lumen 4004. The cord 4006 is freely moveable through the lumen 4004 unless when it is in a locked condition. The cord 4006 is further disposed within the inner housing 4008 having a lumen 4010 running longitudinally therethrough. The inner housing 4008 is disposed within the lumen 4004 of the outer housing 4002 such that the cord 4006 is disposed within the lumen 4010 of the inner housing 4008. In one embodiment, the inner housing 4008 is attached to one side of the outer housing 4002. In another embodiment, inner housing 4008 is mechanically constrained from free longitudinal and rotational movement relative to outer housing 4002. For example, features such as holes, slots, tabs and tangs can be included on the outer housing 4002 and the inner housing 4008 that engage or cooperate with one another to mechanically constrain the inner housing 4008 from longitudinal and/or rotational movement relative to the outer housing 4002.

A locking member 4012 is disposed within the lumen 4004 and over the outer surface of the inner housing 4008. The locking member 4012 is configured to be able to move longitudinally over the cord 4006 and place the cord 4006 in a locked or unlocked condition. In one embodiment, the locking member 4012 is configured to be able to move longitudinally on the outer surface of the inner housing 4008 and place the cord 4006 in a locked or unlocked condition.

In one embodiment, the inner housing 4008 is provided with an opening 4014 laterally cutting through a portion of the inner housing 4008. The opening 4014 cooperates with the locking member 4012 to allow the locking member 4012 to lock the cord 4006 into position or unlock the cord 4006 from a locked condition. The locking member 4012 is disposed on the outer surface of the inner housing 4008 and configured to lock or unlock the cord 4006 through the opening 4014.

In one embodiment, the locking pin 4020 is disposed within the opening 4014. The locking pin 4020, the opening 4014, and the locking member 4012 work together to lock or unlock the cord 4006. To lock or unlock the cord 4006, the locking member 4012 is configured to move longitudinally over the inner housing 4008 (over the outer surface of the inner housing 4008). The moving of the locking member 4012 allows the locking pin 4020 to move up in opening 4014, releasing the cord 4006 or causes the locking pin 4020 to be held down within opening 4014, constraining the cord 4006. The cord 4006 can be placed in a locked condition when the locking pin 4020 is held down by the position of locking member 4012 and the position of the locking pin 4020 restricts the longitudinal motion of cord 4006. The cord 4006 can be placed in an unlocked condition when the position of locking member 4012 is such that locking pin 4020 is free to move up, releasing the cord 4006 and allowing the cord 4006 to move longitudinally freely through the lumen 4010 of the inner housing 4008.

In one embodiment, the opening 4014 created into a portion of the inner housing 4008 exposes the cord 4006. The opening 4014 is perpendicular to the longitudinal axis of the inner housing 4008. The locking pin 4020 sits in the opening 4014. The locking pin 4020 is configured so that it does not lodge into the lumen 4010 of the inner housing 4008. In one embodiment, the locking pin 4020 is configured to be longer than the outer diameter or the width of the inner housing 4008. The locking pin 4020 is also configured to be shorter than the inner diameter of the outer housing 4002 so that its movement is partially constrained by the internal walls of the outer housing 4002. In such configurations, the locking pin 4020 is prevented from lodging into the inner diameter of the inner housing 4008. In one embodiment, the locking pin 4020 resides in the opening 4014 in a way such that it can engage portions of the locking member 4012 and keep the locking member 4012 from longitudinally sliding off the outer surface of the inner housing 4008 in either direction. In other embodiments, the inner housing 4008, the outer housing 4002 and/or the device that the lock device is a part of, attaches to or otherwise communicates with, includes features (e.g., tangs, tabs or other mechanical projections) that constrain the longitudinal motion of the locking member 4012 in a single direction or in both directions. The locking pin 4020 is shown as having a circular cross-section and a rod shape in FIGS. 1A-1B, but, of course, in other embodiments, the locking pin 4020 may have many other cross-sections and shapes without deviating from the scope of the embodiments of the present invention. A circular cross-section helps reduce forces required to operate the locking device 4000 (see later portions of this description for the significance of the forces). A rod shape is the simplest shape to manufacture, as it may be easily formed or cut to the desired length from many materials widely available as preformed wire or rod using common processes.

In one embodiment, the locking pin 4020 is configured to include beveled (pointed) ends 4060 as shown in FIGS. 4 and 6. In this embodiment, instead of having straight cut ends, the locking pin 4020 includes the beveled ends 4060 to provide the locking pin 4020 with the greatest movement range within the lumen 4004. As shown in FIGS. 1A-1B, the locking pin 4020 needs to be able to move up and down within the opening 4014 and relative to the inner diameter of the outer housing 4002 (and inner housing 4008) to cooperate with the locking member 4012 to lock or unlock the cord 4006. When the locking pin 4020 is configured with straight cut ends, the locking pin 4020 would hit the inner wall of the outer housing 4002 and be limited as to its up and down travel distance or range. With the beveled ends 4060, the locking pin 4020 can move up and down with a greater travel distance. In addition, with the beveled ends, the inner diameter (ID) of outer housing 4002 (hence, the outer diameter (OD) of locking device 4000) can be configured to have a smaller dimension than would otherwise be the case when the locking pin 4020 has straight cut ends. In other locking pin 4020 cross-sections, such as those where the interaction of the locking pin 4020 with the opening 4014 prevents the locking pin 4020 from rotating (e.g., a square, rectangular or oval cross-section), a bevel(s), an incline(s) or a curve(s) may be placed on the appropriate side(s) of the end(s) of the locking pin 4020 to facilitate a greater travel distance in the up and/or down direction(s).

Figure 14:
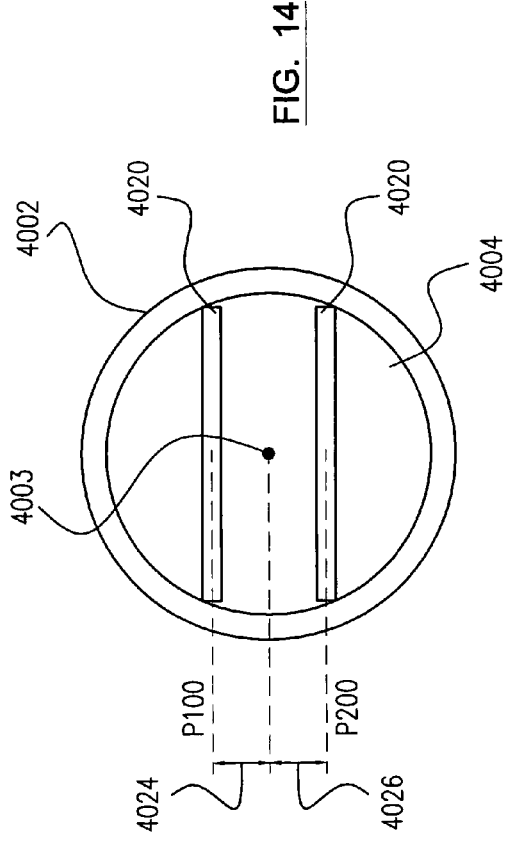
FIG. 14 illustrates an exemplary embodiment of a locking pin included in a cord locking device.

In another embodiment, the inner housing 4008, the opening 4014, the locking pin 4020, the locking member 4012 and the outer housing 4002 are dimensioned such that the locking pin 4020 moves relatively symmetrically up and down in opening 4014 relative to the center point 4003 of the lumen 4004, as shown in FIG. 14. As illustrated in FIG. 14, the locking pin 4020 moves from the center point 4003 up to a position $P_{100}$ and down to a position $P_{200}$. From the center point 4003, the locking pin 4020 moves a distance 4024 upward and a distance 4026 downward. The distance 4024 and the distance 4026 are substantially equal to one another. Thus, the maximum distance that the locking pin 4020 can move within opening 4014 is substantially equal to the maximum distance that the locking pin 4020 can move up and down relative to the center point 4003 of the lumen 4004 (as constrained by the ID of the outer housing 4002/the lumen 4004 and, in some configurations, the dimensions of the opening 4014 and/or the dimensions of the locking member 4012). Using such configurations, the ID of the outer housing 4002 (lumen 4004) may be minimized and, hence, the OD of the locking device 4000 may be minimized for any desired travel range of the locking pin 4020. This minimization may allow the locking pin 4020 to have straight ends, as shown in FIG. 14, in a locking device 4000 with an acceptably small OD. Straight cut ends on small parts like the locking pin 4020 may be simpler and more economical to fabricate. Additionally, straight cut ends on the locking pin 4020 may engage the locking member 4012 more reliably than inclined or beveled ends.

In one embodiment, as shown in FIGS. 1A-1B, 3, and 5, the locking member 4012 is disposed on the outer surface of the inner housing 4008 partially filling at least a portion of the gap between the inner surface of the outer housing 4002 and the outer surface of inner housing 4008. The locking member 4012 is slightly smaller than the dimensions of the gap between the inner surface of the outer housing 4002 and the outer surface of inner housing 4008, so that the locking member 4012 may slide freely longitudinally within this gap. In addition, the locking member 4012 is captured from moving longitudinally off of the outer surface of the inner housing 4008 and out of the inside of the locking device 4000 by its engagement with the protrusions of the locking pin 4020 on either side of the inner housing 4008 (see FIGS. 1A-1B).

The locking member 4012 includes an incline 4016 and an indent 4018 on each side of the locking member 4012. The indent or detent 4018 is configured so that it can engage the locking pin 4020 to limit the motion of the locking pin 4020, such that the locking pin 4020 is held near or against the bottom of opening 4014 of the inner housing 4008 and/or in contact with or close to the ID of the outer housing 4002. The incline 4016 is configured such that at its upper limit, it may constrain the locking pin 4020 from moving up and out of the opening 4014 and/or allow the locking pin 4020 to be constrained by its contact with the ID of the outer housing 4002.

The cord 4006 may be very flexible or very stiff and anywhere in between, as desired for the application and as designed. In one embodiment, the cord 4006 is composed of a metallic wire or wires, such as stainless steel or nickel titanium. In another embodiment, the cord 4006 is composed of a polymer or polymeric filaments, such as a silicone, a polyurethane, a fluorocarbon or Kevlar® (poly(p-phenylene-terephtalamide)); Kevlar is a registered trademark of Dupont). In another embodiment, the cord 4006 is composed of a combination of metallic and/or polymeric wires and/or filaments. In another embodiment, the cord 4006 is coated with a polymeric coating.

In one embodiment, the cord 4006 includes one or more interferences 4022. The interference 4022 can be bumps created on the outer surface of the cord 4006. In this embodiment, the cord 4006 can be composed of or coated with a low friction and relatively stiff material such as Nylon, Polyethylene (PE), Polytetrafluoroethylene (PTFE) or Polyetheretherketone (PEEK). In one embodiment, an interference 4022 is created by shrink melting sections of a miscible material into the coating of or directly into the cord 4006. In one embodiment, shrink melting sections of nylon tubes onto the nylon coating of the cord 4006 or the cord 4006's coating creates the interferences 4022. In another embodiment, tubes or other shapes with a compatible inner diameter are placed over the outer diameter of the cord 4006 and crushed, welded, soldered, brazed, glued or crimped in place to form the interferences 4022 on the outside of the cord 4006. In another embodiment, the interferences 4022 are molded onto the surface of the cord 4006 or a coating of the cord 4006. In one embodiment, the interferences 4022 have curved, inclined or beveled ends to aid in the smooth movement of the cord 4006 through the locking device 4000. These type of ends on the interference 4022 also aid in providing forces that help retain the locking pin 4020 in the indent or detent 4018 (and thus help assure that the locking device 4000 will remain locked) when an interference 4022 is forced up against the locking pin 4020 in the locked condition by the forces acting on the cord 4006.

In one embodiment, in the locked condition, the interferences 4022 will cause a mechanical interference with the locking pin 4020 to the section of the cord 4006 that has the interferences 4022 such that, when the locking pin 4020 engages the interferences 4022, the cord 4006 is locked into a position between the interferences 4022 or against an interference 4022 and the cord 4006 is not allowed to freely move longitudinally in at least one direction within the inner housing 4008.

In alternative embodiments, the cord 4006 may include a section or sections of materials, which may be at relatively the same OD, along its length, but with different moduli and/or different friction characteristics to provide similar functions as those of the interferences 4022 (FIGS. 2A-2B). The locking device 4000 shown in FIGS. 2A-2B is the locking device 4000 shown in FIGS. 1A-1B except that the cord 4006 does not include the interferences 4022. As shown in FIGS. 2A-2B, the cord 4006 has the same OD across the entire length of the cord 4006. In addition, the cord 4006 has one or more sections 4007 that have high friction characteristics. In some embodiments, the cord 4006 may be coated with a material to provide the friction characteristics. In addition, the cord 4006 may include sections 4007 that are relatively deformable to allow the locking of the cord 4006. As shown in FIGS. 2A-2B, when a locking pin 4020 is pressed down onto the cord 4006, (e.g., as an actuator 4028 is forced in the D100 direction to move the locking member 4012 in the D100 direction), the particular section of the cord 4006 is pinched and pressed against the inner surface of the inner housing 4008. The cord 4006 is thus locked into position.

In some embodiments, the cord 4006 contains a resilient interference 4022 or other larger OD section that is positioned such that during the shipment and prior to use of the device incorporating the lock device 4000, this section resides under the locking pin 4020 and provides an increased force against the locking pin 4020 and, thus, further ensures that unusual shocks and vibrations can't cause the locking member 4012 to move such that the locking pin 4020 becomes free of the indent or detent 4018, placing the lock device 4000 in an undesired unlocked condition.

In the unlocked condition, as the cord 4006 with interferences 4022 is moved relative to the locking device 4000, the cord 4006 moves through the lumen 4010 of the inner housing 4022. When the locking pin 4020 encounters an interference 4022, the locking pin 4022 is pushed up against the incline 4016 of the locking member 4012. The force of the locking pin 4002 against the incline 4016 creates a force that acts to move the locking member 4012 longitudinally in a manner that uncovers more of opening 4014. The locking member 4012 is thus forced toward the position shown in FIG. 1A or FIG. 3. The locking pin 4022 is thus able to be pushed up enough toward or against the incline 4016 to allow the interference 4022 to pass through in either direction of the locking member 4012. The dimensions of the cord 4006 and those of the locking device 4000 are chosen such that the locking pin 4020 encounters the cord 4006, even at the cord's 4006 smallest outer diameter, prior to the locking pin 4020 being able to reach a level that would allow the locking pin 4020 to engage the indent or detent 4018 of the locking member 4012. Thus, in the unlocked condition, the locking pin 4020 is confined to the inclined area 4016 of the locking member 4012 by the presence of the cord 4006 and the cord 4006 may move relatively freely in and out of the locking device 4000.

In some embodiments, the cord 4006 contains an interference 4022 or other larger OD section that is positioned such that during the shipment and prior to use of the device incorporating the lock device 4000, this larger OD section resides under the locking pin 4020 and, thus, further ensures that unusual shocks and vibrations can't induce an undesired locked condition. In some embodiments, the cord 4006 includes an interference 4022 or other larger OD section that is positioned such that the locking of the device in undesired cord 4006 positions is prevented. In some embodiments, the cord 4006 includes an interference(s) 4022, a loop (not shown), an attached component near its proximal end or other mechanism on or near its proximal end to accommodate the releasable pulling of the cord 4006. In some embodiments, the cord 4006 includes an interference 4022, a loop (not shown), an attached component near its proximal end or other mechanism on or near its proximal end whose OD is too great to pass through the inner housing 4008 under any encountered condition, whether locked or unlocked, and, thus, prevents the portion of the medical or other device attached to the other end of the cord 4006 from being detached from the portion of the medical device or other device that incorporates the lock device 4000.

In one embodiment, an actuator 4028 is used to move the locking member 4012 to lock and/or unlock the cord 4006 relative to the locking device 4000. The actuator 4028 can be a small pin, a small wire, or a guidewire-like device typically used with a catheter assembly. The actuator 4028 should have sufficient rigidity to allow it to exert sufficient force on the locking member 4012 to push the locking member 4012 longitudinally over the outer surface of the inner housing 4008. In one embodiment, the actuator 4028 is pressed against the locking member 4012, thus causing the locking member 4012 to move in a desired direction along the outer surface of the inner housing 4008. In such an embodiment, the actuator 4028 is inserted into an opening (e.g., the lumen 4004) of the outer housing 4002 to contact the locking member 4012 to cause the locking member 4012 to move. As shown in FIG. 5, pushing by the actuator 4028 will cause the locking device 4000 to change from the unlocked to the locked condition. It should be noted that the longitudinal orientation of the locking member 4012 within the locking device 4000 may be reversed, such that pushing by the actuator 4028 will cause the locking device 4000 to change from the locked condition to the unlocked condition. In some embodiments, where the locking device 4000 is not part of a device that must be detached, the actuator 4028 may be attached to, constrained by or an extension of the locking member 4012. In this case, the locking member 4012 may be moved in either direction to the locked or unlocked condition as desired.

Figure 7:
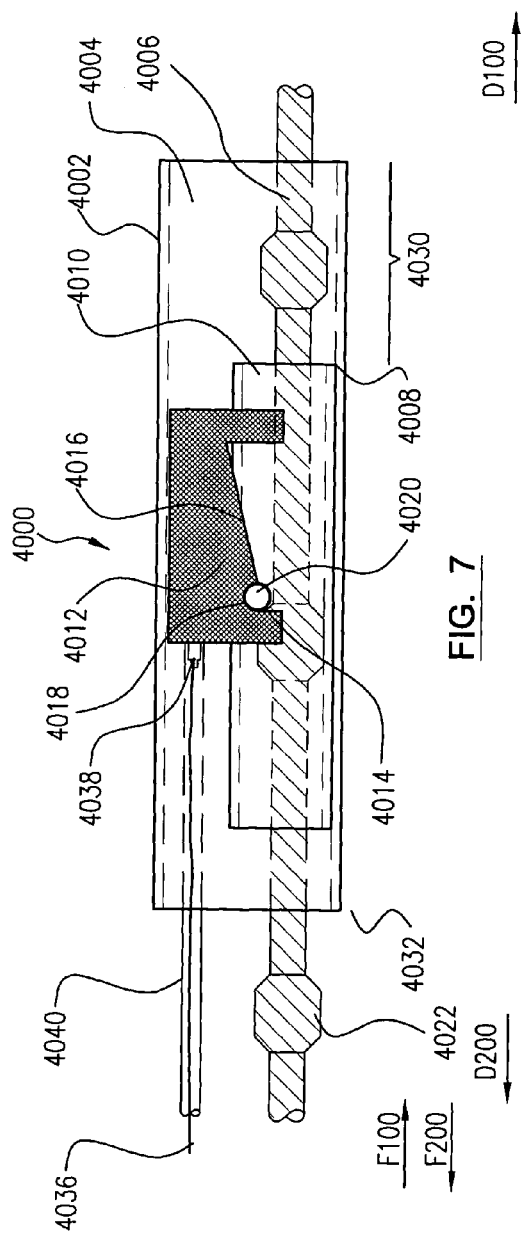
FIGS. 7-8 illustrates an exemplary embodiment of an engagement member included within a locking device.
Figure 8:
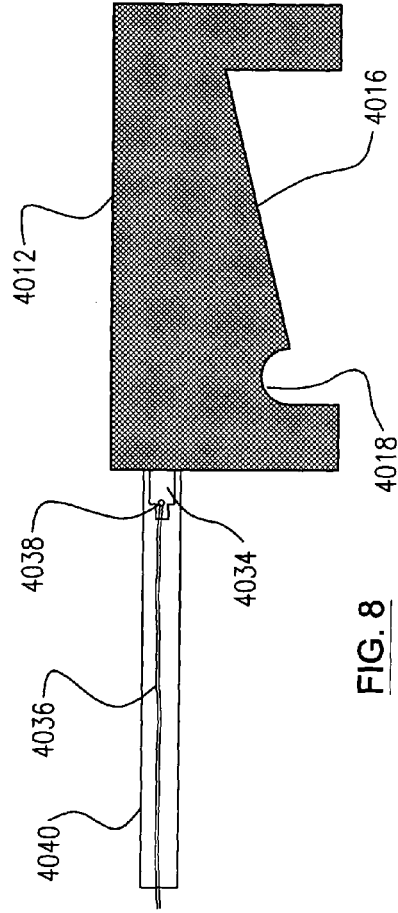

In another embodiment, the actuator 4028 is removably coupled to the locking member 4012 to facilitate the moving of the locking member 4012. In some cases, the locking member 4012 may need to be moved back and forth to allow additional flexibility in adjusting the position of the cord 4006 either before or after locking or unlocking the cord 4006. Thus, the locking member 4012 needs to be moved in both forward and backward directions (e.g., $D_{100}$ and $D_{200}$ directions). In one embodiment, as shown in FIGS. 7-8, an actuator 4040 is coupled to the locking member 4012 through an engagement member 4034 provided on the locking member 4012. The engagement member 4034 can be a protrusion or an extension feature provided on one side of the locking member 4012 as shown in FIGS. 7-8. In addition, the engagement member 4034 further includes an opening or a loophole 4038. The engagement member 4034 is configured so that it can mate with the actuator 4040 and couple the actuator 4040 to the locking member 4012. The actuator 4040 can be a small tube having a lumen running therethrough. The actuator 4040 is configured to fit over the engagement member 4034 to allow the actuator 4040 to move the locking member 4012. In one embodiment, the actuator 4040 is provided with a thread 4036 (e.g., a Kevlar® thread) disposed within the lumen of the actuator 4040 and looped through the opening 4038 of the engagement member 4034. With such configurations, exerting a force $F_{100}$ on the actuator 4040 will move the locking member 4012 in the direction of the force (e.g., direction $D_{100}$) and pulling on the thread 4036 with a force $F_{200}$ will cause the locking member 4012 to move in the direction of the force $F_{200}$ (e.g., direction $D_{200}$). The actuator 4040 can be removed from the engagement member 4034 and the thread 4036 removed from the opening 4038 when the locking member 4012 is placed in a desired final location. Such configurations allow the locking member 4012 to be moved in either direction to facilitate the adjustment of the cord 4006. Allowing adjustment for the cord 4006 provides flexibility and adjustments for the particular device that is coupled to the locking device 4000.

In another embodiment, as shown in FIGS. 9-10, an actuator 4044 is coupled to the locking member 4012 through an engagement member 4042 provided on the locking member 4012. The engagement member 4042 can be a protrusion or an extension feature provided on one side of the locking member 4012 as shown in FIGS. 9-10. In addition, the engagement member 4042 further includes a threaded section 4046. The engagement member 4042 is configured so that it can mate with the actuator 4044 having a complimentary threaded section 4048 to couple the actuator 4044 to the locking member 4012. The actuator 4044 can be a small wire having a male threaded section 4018 while the engagement member 4042 can have a female thread section 4046. Alternatively, the actuator 4044 can be a small member having a female threaded section 4048 while the engagement member 4042 can have a male thread section 4046. With such configurations, exerting a force $F_{100}$ on the actuator 4044 will move the locking member 4012 in the direction of the force (e.g., direction $D_{100}$) and pulling on the actuator 4044 with a force $F_{200}$ will cause the locking member 4012 to move in the direction of the force $F_{200}$ (e.g., direction $D_{200}$). The actuator 4044 can be removed (by unscrewing) from the engagement member 4042 when the locking member 4012 is placed in a desired location. In alternate embodiments, there may be no protrusion of engagement member 4042, the female threaded section 4048 may reside inside the locking member 4012 or the positions of the male and female threads reversed. Such configurations allow the locking member 4012 to be to be moved in either direction to facilitate the adjustment of the cord 4006. Allowing the locking member 4012 to be moved in both directions provides additional flexibility, reversibility of adjustments and reversibility of locking or unlocking for the particular device that is coupled to the locking device 4000.

It is appreciated that the actuator can be coupled to the locking member 4012 in many other ways such as adhesive, soldering, and welding.

In one embodiment, the inner housing 4008 is attached to the inner diameter of the outer housing 4002. The outer housing 4002 and the inner housing 4008 can be made using stainless steel hypotubes and be soldered together along the line of their contact with each other. Of course, various forms of welding, brazing and adhesives may also be used to couple the inner housing 4008 to the outer housing 4002. In addition, laser or electric welding can also be used to attach the inner housing 4008 to the outer housing 4002. In some embodiments, the outer housing 4002 and the inner housing 4008 are made of plastics, and they may be extruded and bonded/joined/formed/fused in the many ways conventionally used to join plastics together.

In other embodiments, the outer housing 4002 may be configured to include features such as cut(s), slot(s) and/or hole(s) (not shown) at or near a desired line/position of attachment with the inner housing 4008 to facilitate the joining process.

The outer housing 4002 may be made longer than the inner housing 4008 to provide attachment and/or engagement areas for other devices or parts of devices. In FIGS. 1, 2, 3, and 5, the locking device 4000 is shown with an attachment area 4030 and an engagement area 4032. In one embodiment, an attachment area refers to an area of the locking device 4000 reserved for a particular device to be coupled to the locking device 4000. The attachment area 4030 may be formed or adapted to be an integral part of the device that incorporates the lock device 4000. Typically, the attachment of the particular device and the locking device 4000 is permanent (at least during the course of use) so that the locking device 4000 can lock and/or unlock a cord in the particular device. In one embodiment, an engagement area refers to an area of the locking device 4000 reserved for a particular delivery device (e.g., a delivery catheter) to be engaged to the locking device 4000. The engagement of the particular delivery device to the locking device 4000 may be temporary during the delivery time. The delivery device may be disengaged from the locking device 4000 after the device incorporating the locking device 4000 is delivered into position.

In one embodiment, the attachment area 4030 is located on the distal end of the outer housing 4002 and the engagement area 4032 is located on the proximal end of the outer housing 4002. Devices may be attached to or engaged with the outer housing 4002 through the outer areas of the attachment area 4030 and the engagement area 4032 or alternatively or in addition, through the inner areas of the attachment area 4030 and the engagement area 4032.

Figure 11:
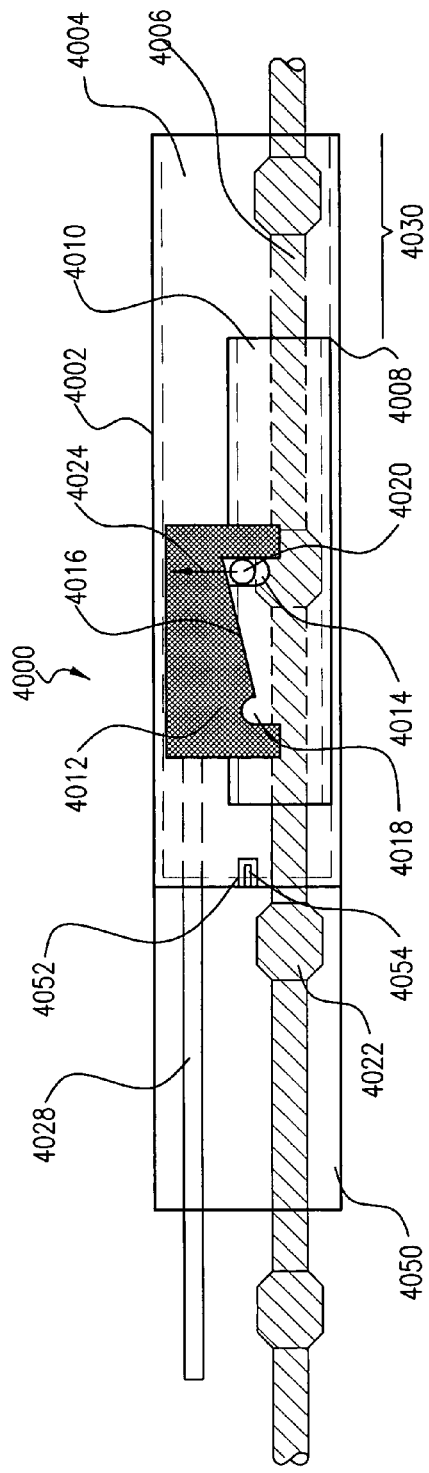
FIGS. 11-13 illustrates an exemplary embodiment of an alignment and engagement of the locking device and a delivery device.
Figure 12:
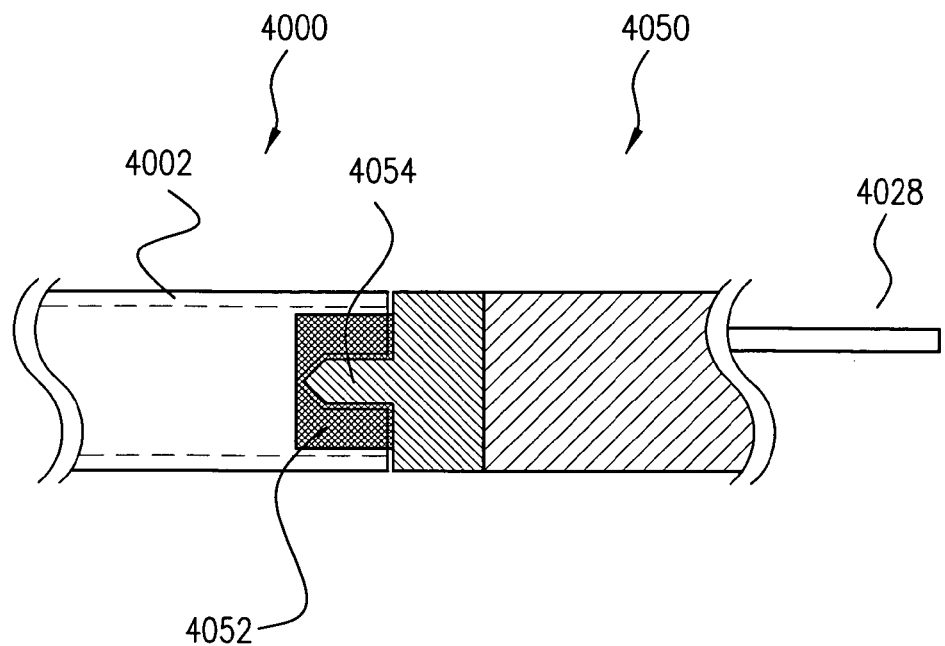
Figure 13:
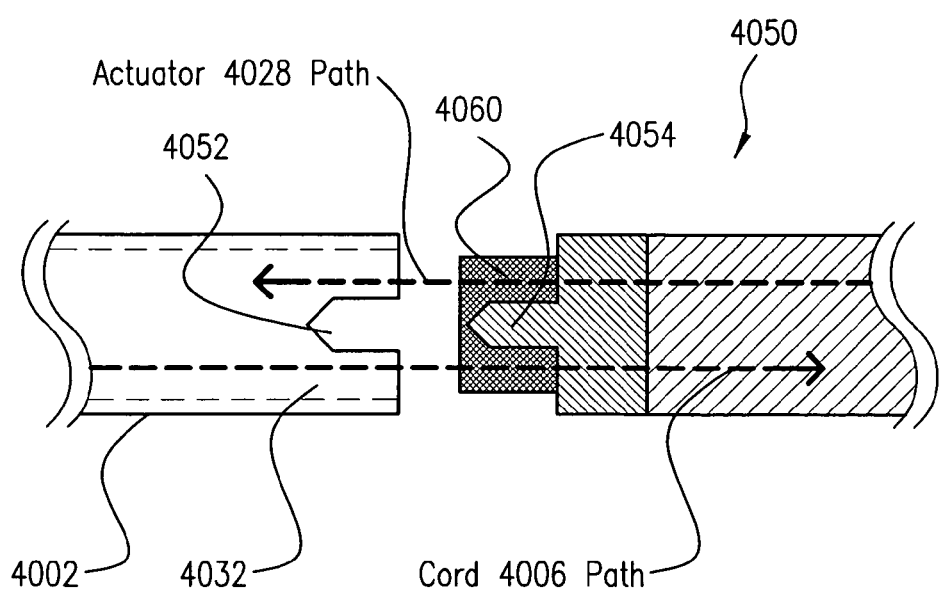

In one embodiment, each of the attachment area 4030 and the engagement area 4032 may include an alignment feature 4052 (shown in FIGS. 11-13) to maintain a proper alignment of the locking device 4000 relative to the devices that are to be attached to and/or engaged with the locking device 4000. As shown in FIGS. 11-13, the outer housing 4002 includes one or more alignment features 4052 (e.g., two alignment features 4052). The device to be engaging with the outer housing 4002 of the locking device 4000, for example, a delivery device 4050 or a delivery catheter 4050, includes one or more complimentary alignment features 4054 that will align with the alignment feature 4052. As is known, there are many ways to configure the alignment features 4052 or 4054. In one embodiment, either the alignment feature 4052 or the complimentary alignment feature 4054 can be a carved section where the other one can be a notch that fits into the carved section. Properly aligning the device 4050 relative to the locking device 4000 ensures proper alignment of the locking device 4000 and the actuator 4028 that extends out of device 4050 and is used to actuate the locking member 4012 of the locking device 4000 as previously discussed. Properly aligning the device 4050 relative to the locking device 4000 also ensures the proper alignment of cord 4006 and/or any cord pulling mechanism or cord accommodating lumen of the device 4050 with the exit of the cord 4006 from the locking device 4000. In one embodiment, to further aid in the desired alignment, the device 4050 is provided with a complimentary engagement area 4060 that engages the ID of the outer housing 4002 with a slip fit in the engagement area 4032 and butts up against the proximal end of the outer housing 4002, as shown in FIGS. 12-13. This form of engagement allows the delivery device 4050 to apply a force to the outer housing 4002 (or locking device 4000) to balance any forces applied to the cord 4006 such that the locking device 4000 (and any device which is attached to it) may be maintained in a relatively stable position during cord 4006 adjustments. This form of engagement also allows the delivery device 4050 to disengage from the locking device 4000 when the cord 4006 is released after adjustment and locking. This form of engagement also ensures that the distal end of the delivery device 4050 is in longitudinal alignment with the locking device 4000 to ensure the smooth operation and movement of the locking device 4000, the cord 4006 and the actuator 4028. In other embodiments, the OD of the outer housing 4002 may be engaged or similar engagement and/or alignment configurations may be employed in attachment area 4030.

In one embodiment, as the locking member 4012 is actuated by the actuator 4028, (e.g., from the position shown in FIG. 1A to the position shown in FIG. 1B), the locking member 4012 is moved in the direction of the force $F_{100}$. As the locking member 4012 moves, the locking pin 4020 is forced down along the incline 4016 causing the locking pin 4020 to engage the indent/detent 4018. The locking pin 4020 is then forced to move to a lower position along the opening 4014. In one embodiment, as the locking pin 4020 is moved to a lower position, the locking pin 4020 engages the cord 4006 and the cord 4006 exerts force up onto the locking pin 4020, which ensures that the locking pin 4020 will remain in the indent/detent 4018 (unless sufficient force is applied to the locking member 4012 in the proper direction). In one embodiment the force exerted on the cord 4006 against the inner surface of the inner housing 4008 (or in some embodiments the inner surface of the outer housing 4002) by the locking pin 4020 in the indent/detent 4018 is sufficient to provide enough friction to lock the cord 4006 in place. In another embodiment, this force is not sufficient to lock the cord 4006, so the cord 4006 is provided with the interferences 4022 that will mechanically engage and interfere with the locking pin 4020 in the indent/detent position as the cord 4006 is pulled in either direction and, thus provide sufficient locking forces. In this embodiment, it may be desirable to move the cord 4006 longitudinally a short distance while applying force F100 to the locking member 4012 to ensure that the locking pin 4020 is between the interferences 4022 when it enters the indent/detent 4018 and/or that a minimum or practical applied force F100 will be required to ensure that the locking pin 4020 enters the indent/detent 4018.

In another embodiment, as the locking pin 4020 is moved to a lower position, the locking pin 4020 engages the bottom of opening 4014 and the components of the locking device 4000 deform as the locking pin 4020 enters indent/detent 4018. The forces generated by this deformation ensure that the locking pin 4020 will remain in the indent/detent 4018 (unless a sufficient force is applied to the locking member 4012 by an actuator in the proper direction). Of course, as described above, the cord 4006 in this embodiment may or may not be provided with interferences 4022, as required, to provide desired cord 4006 locking forces.

To unlock the cord 4006, the locking member 4012 may be moved in the opposite direction of the force $F_{100}$, e.g., direction $D_{200}$. In one embodiment, the actuator 4028 is pulled in the direction $D_{200}$ to move the locking member 4012. Moving the locking member 4012 in the direction of $D_{200}$ causes the locking pin 4020 to be disengaged from the indent/detent 4018. Without the indent/detent 4018 restricting the movement of locking pin 4020 up in the opening 4014, the cord 4006 can be freely moved within the inner housing 4008. The cord 4006 is thus unlocked as shown in FIG. 1A.

In one embodiment, the locking member 4012 with the incline 4016 provides a mechanical advantage that multiplies the force $F_{100}$ applied to the actuator 4028 and applies it to the cord 4006, deforming the cord 4006 and/or lock device 4000 and allowing the locking member 4012 to continue to move distally to cause the locking pin 4020 to move into the indent/detent 4018. When the locking pin 4020 is over an interference 4022 of the cord 4006 (as when the interference is beneath the opening 4014), pulling the cord 4006 slightly in either direction $D_{100}$ or $D_{200}$ until the locking pin 4022 is over a smaller OD portion of the cord 4006, while applying the force $F_{100}$, will cause the locking pin 4020 to engage the indent/detent 4018. Once the force $F_{100}$ is removed, the locking pin 4020 will remain in the indent/detent 4018 because of the force applied to it by the cord 4006 and/or the deformation of the lock device 4000. In this embodiment, the force between the cord 4006 and the locking pin 4020 to keep the force $F_{100}$ required to move the locking pin 4020 into the indent/detent 4018 is very small. Because the force between the cord 4006 and the locking pin 4020 is small, there is little friction between the locking pin 4020 and the small OD portions of cord 4006, so if the cord 4006 is pulled in direction $D_{100}$ (or the opposite direction) relative to the locking device 4000, the cord 4006 will slip on its small OD portions relative to the locking pin 4020 at a small applied pull force. However, when the locking pin 4020 encounters an interference 4022 on the cord 4006, a larger pull force on the cord 4006 can be applied with little relative movement, because the indent/detent 4018 constrains the locking pin 4020 too close to the internal wall of the inner housing 4008 (or, in some configurations, the internal wall of the outer housing 4002) for the interference 4022 to pass. Without much force (pulling or pushing) on either the actuator 4028 or the cord 4006 after the locking pin 4020 engages the indent/detent 4014, the cord 4006 is locked into position relative to the locking device 4000. In a similar manner, the configuration and interaction of the indent or detent 4018 and the locking pin 4020 can be adjusted to limit the force required to unlock the cord 4006.

In other embodiments, where applied force $F_{100}$ can be larger, the friction force that is required to lock the cord 4006 into position may be obtained without the need of interferences 4022. In an alternative embodiment, instead of the interferences 4022, a deformable coating is applied to the cord 4006 or the cord 4006 itself is a suitably deformable structure (e.g., FIGS. 2A-2B). The locking pin 4020 can exert a force over any portion of the cord 4006 to deform the cord 4006 at that portion in order to lock the cord 4006 in position. The locking pin 4020 thus can press down onto the cord 4006 and onto the deformable coating/structure, which allows the locking pin 4020 to hold the cord 4006 in position by pinching the cord 4006 against the inner wall of the inner housing 4008 (or, in some configurations, the internal wall of the outer housing 4002). The deformable coating/structure may contain a relatively high friction type of resilient material such as a polyurethane, ionomer or silicone to help limit the required applied force.

In embodiments where the inner housing 4008 and the outer housing 4002 are soldered together, the locking pin 4020 and the locking member 4012 may be made out of materials that are not easily affected by the soldering process used for the housings such as titanium or nickel titanium. Such materials do not easily wet with the soldering material that may be used for stainless steel housings (e.g., silver-tin) because its oxide layer does not get etched by the flux used for soldering stainless steel. Thus, the soldering material will not wick onto the locking pin 4020 and the locking member 4012 and cause them to be attached to the inner housing 4008 or the outer housing 4002 when the soldering material cools. In addition, this helps ensure that the locking pin 4020 and the locking member 4012 are free to move within the locking device 4014.

Figure 15:
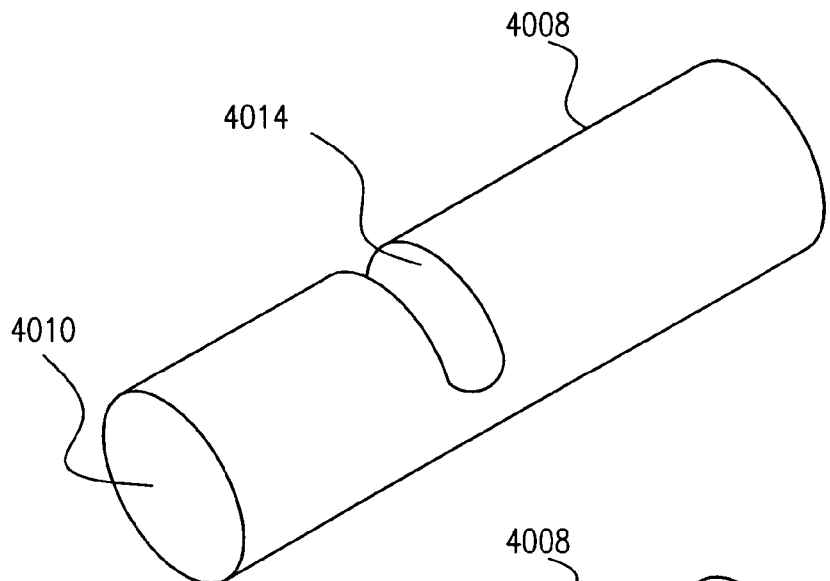
FIGS. 15-18 illustrate an exemplary process of making a cord locking device in accordance to exemplary embodiments of the present invention.
Figure 16:
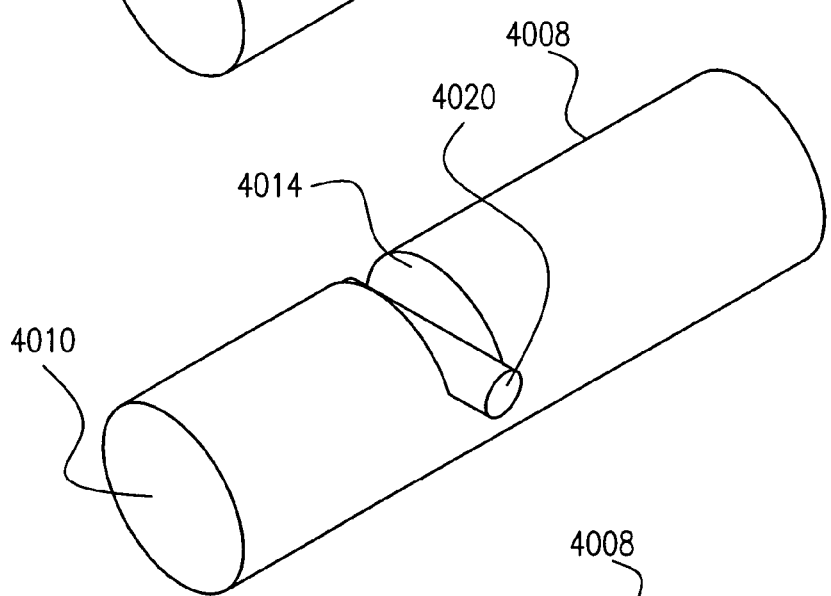

FIGS. 15-18 illustrate an exemplary process and the resulting structures of making the locking device 4000. In FIG. 15, an inner housing 4008 is provided. The inner housing 4008 includes a lumen 4010 and an opening 4014. The opening 4014 is cut perpendicularly to the longitudinal axis of the inner housing 4008. In FIG. 16, a locking pin 4020 is disposed within the opening 4014. As previously discussed, the locking pin 4020 and the inner housing 4008 are dimensioned so that the locking pin 4020 will not lodge into the lumen 4010. The locking pin 4020 is freely disposed within the opening 4014 and is allowed to move up and down along the opening 4014.

Figure 17:
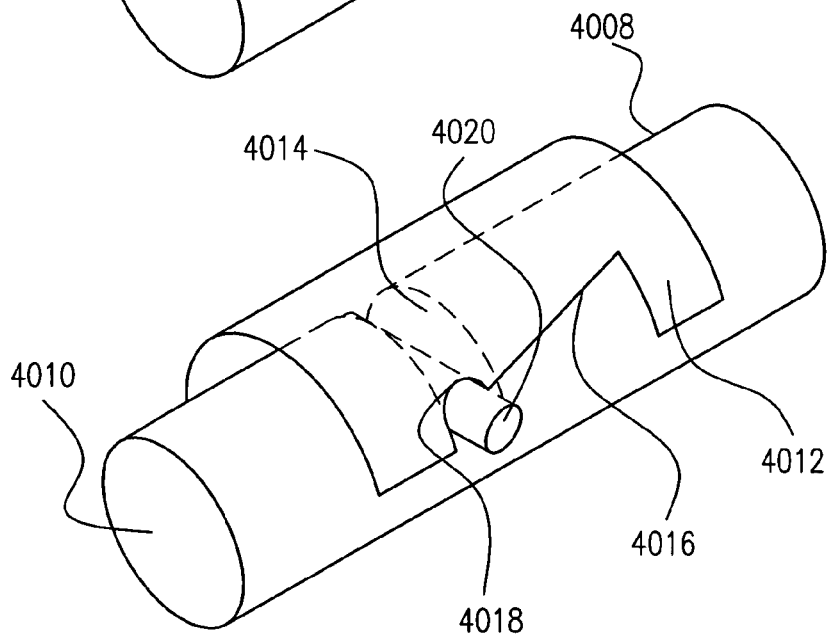

In FIG. 17, a locking member 4012 is placed on the outer surface of the inner housing 4008. The locking member includes an incline 4016 and an indent 4018 positioned at the lower portion of the incline 4016. In one embodiment, the indent 4018 is cut perpendicularly into the incline 4016 portion of the locking member 4012. When the locking member 4012 is placed over the inner housing 4008, the locking pin 4020 will work to prevent the locking member 4012 from sliding off the inner housing 4008. The locking pin 4020 may engage the indent 4018 or slide along the incline 4016 depending on the position of the locking member 4012.

Figure 18:
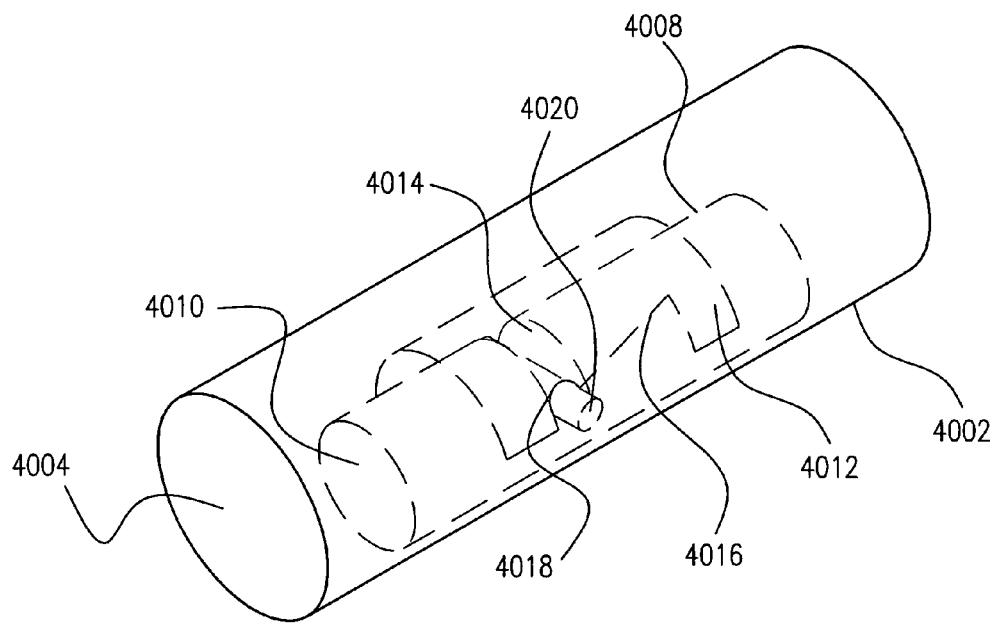
Figure 19:
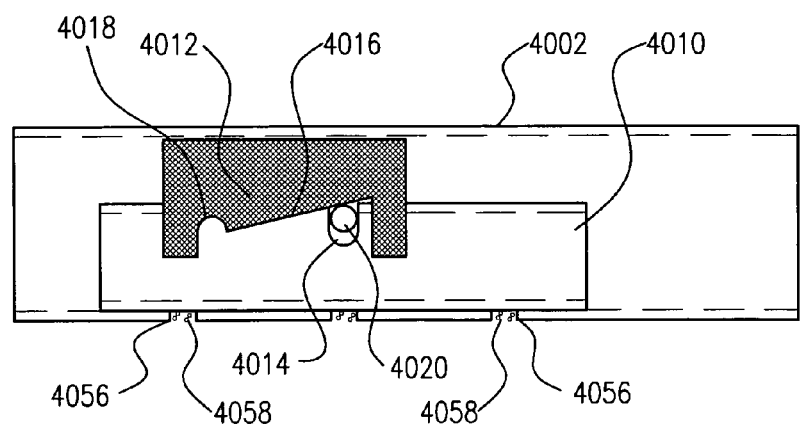
FIG. 19 illustrates an exemplary method of coupling an inner housing of a cord locking device to an outer housing of a cord locking device.

In FIG. 18, the whole assembly, the inner housing 4008 with the locking member 4012 is placed within a lumen 4004 of an outer housing 4002. In one embodiment, the inner housing 4008 is attached to the outer housing 4002 on one side. In this embodiment, the inner housing 4008 can be attached to the outer housing by soldering, welding, brazing, adhesives, or other convenient methods. In one embodiment, the inner housing 4008 is soldered to the outer housing 4002 at an area where the outer diameter of the inner housing 4008 touches or contacts the inner diameter of the outer housing 4002. A soldering flux can be disposed into this area and heat is applied to solder the inner housing 4008 to the outer housing 4002. In another embodiment, one or more openings 4056 is created on the outer housing 4002 (FIG. 19) to facilitate the attachment of the inner housing 4008 to the outer housing 4002. The openings 4056 allow the soldering flux to be disposed or wicked therethrough into the area where the inner housing 4008 and the outer housing 4002 are in close proximity or they contact or touch. In other embodiments, various welding processes may be used to attach the inner housing 4008 to the outer housing 4002.

In another embodiment, the inner housing 4008 is not attached to outer housing 4002; however, its motion relative to the outer housing is appropriately constrained. Without the attachment of the inner housing 4008 to the outer housing 4002, the locking mechanism (designed as previously described) is already constrained within the inner surface of the outer housing 4002, such that it may only freely rotate and longitudinally translate within the lumen 4004. Thus, the inner housing 4008 need only be constrained against this rotation and translation within the lumen 4004. There are various designs and processes that can create this constraint. In one embodiment, a piece of a compatible material can be sized to be attached (soldered, welded, glued, fused, etc.) to the outer wall of the inner housing 4008 through one or more openings 4056 in the outer housing 4002. This attached piece of material would then interfere with the sides of the opening 4056 and constrain the translation and rotation of the inner housing 4008 relative to the outer housing 4002 within the desired limits. The soldering embodiment of this method is to first tin (apply a very thin coat of solder to) the appropriate area of the inner housing 4008. Then the locking mechanism is positioned inside the outer housing 4002. Without flux, solder is then applied to the inner housing 4008 through opening(s) 4056. This creates a solder ball attached to the tinned portion of the inner housing 4008 that partially fills opening(s) 4056, but is not attached to the outer housing 4002. A variation of this embodiment is to construct the outer housing 4002 out of a material that is unaffected by the flux and/or will not be wetted by the solder used.

In another embodiment, the piece(s) of material is first attached to the outer housing 4002. The locking mechanism is then assembled and forced into the inner housing 4008, temporarily deforming the components of the locking device 4000 until the piece(s) of material encounters the desired opening(s) 4056 and moves into it (them). This creates the same constraint situation as the previous embodiment, but is assembled in a method that is commonly referred to as a snap fit. In other snap fit embodiments, there may be no attached material piece(s) and the constraining material(s) may be a tang(s) or tab(s) cut from and bent away from the inner housing 4008 or a deformation(s) of the inner housing 4008. In other snap fit embodiments, the constraining material(s) may be attached to or a deformed part of the outer housing 4002 and the inner housing 4008 will incorporate the mating opening(s) 4056 or other mating feature(s). The designs for material pieces or projections to facilitate a snap fit and appropriately constrain parts are well known in the art. A snap fit design has the advantages of being very easy and fast to assemble and of being very reliable and easy to inspect, unlike welds, brazing or soldering.

The locking device 4000 has several advantages. The locking device can be effectively and functionally made to be very small and with a circular cross-section. The locking device 4000 thus, can be easily incorporated into are delivery device such as an intravascular catheter. In addition, the locking device 4000 can be actuated with a very small force that can be applied by a wire (to act as the actuator 4028) via a catheter lumen (such as one provided with a delivery catheter). Furthermore, a guidewire (typically used in a delivery catheter) sized or smaller wire can be configured to function as the actuator 4028 to actuate the locking device. The locking device 4000 can be made small to be easily adapted to a catheter assembly and to minimize the impact of a locking device on the size of the catheter assembly.

In one embodiment, the locking device 4000 also provides a way of making an in situ length adjustments for a medical device. For instance, the cord 4006 can be an integral part of the cord of the medical device that is configured to adjust the length or width of that medical device. After the adjustment is complete, the cord 4006 is locked into position as previously described to maintain the length and/or width of the medical device. The adjustment can be done in situ with the device delivered to appropriate location.

In one embodiment, the locking device 4000 is used to lock the position of a cord relative to the locking device 4000. For instance, the locking device 4000 can be used to lock a cinching cord in a Mitral valve regurgitation percutaneous annuloplasty device described in U.S. patent application Ser. No. 10/297,714 previously incorporated. In one embodiment, the locking device 4000 is mounted on the proximal end of the annuloplasty device. In another embodiment, the locking device 4000 is incorporated into a medical device having an implantable member that is actuated by a cord (e.g., an annuloplasty device, a deflectable device, an implantable device, etc.). The locking device 4000 can be coupled to a proximal end of the medical device or can be an integral part of the medical device. The cord of the locking device 4000 can be the cord that is part of the implantable member and the distal end of the cord can be attached to at least a portion of the implantable member.

In one embodiment, the locking device 4000 is incorporated into an annuloplasty device that can be used to treat medical conditions such as defective or faulty heart valves. The annuloplasty device can be used to treat a faulty heart valve such as those seen in mitral valve regurgitation. The annuloplasty device can reduce the cross-sectional size of the annulus of the mitral valve or bring the leaflets of the valves closer to each other. For example, the annuloplasty device can move the posterior annulus of the mitral valve toward the anterior annulus of the mitral valve. Alternatively, the annuloplasty device can reshape the cross-sectional size of the mitral valve annulus. Reshaping includes at least one of reducing, reforming, or adjusting the mitral valve annulus in ways that cause the leaflets of the mitral valve to move closer to each other. Reshaping may also include increasing the curvature (or reducing the radius along at least a portion of the curvature) of the coronary sinus that substantially encircles that mitral valve annulus thereby reshaping the mitral valve or the mitral valve annulus. Reshaping may also include decreasing the curvature (or increasing the radius along at least a portion of the curvature) of the coronary sinus in a way that exerts pressure on the mitral valve annulus or the mitral valve and flattening a portion or a side of the mitral valve annulus or the mitral valve.

Figure 20:
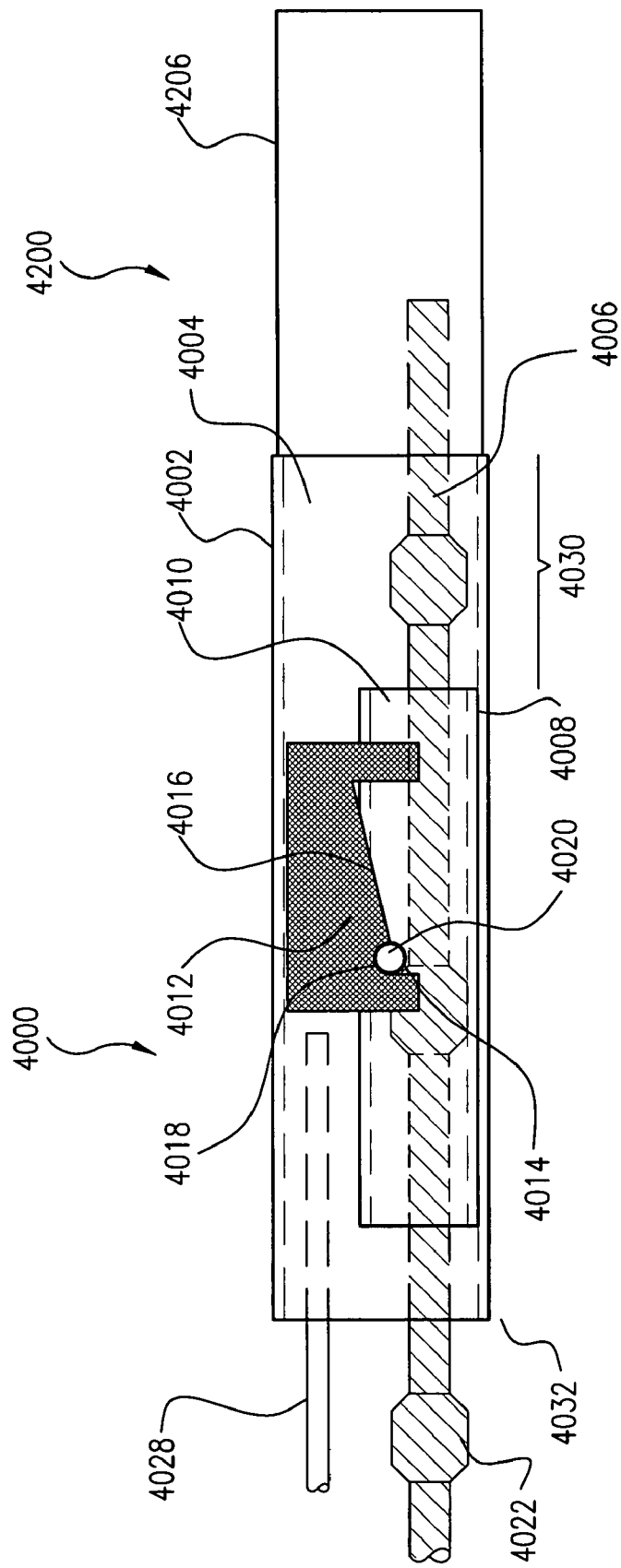
FIG. 20 illustrates an exemplary medical device that includes an implantable device coupling to a locking device.

FIG. 20 illustrates an exemplary embodiment of a medical device 4200 that includes the locking device 4000 as previously described and an implantable device 4206 such as an annuloplasty device previously described in the U.S. patent application Ser. No. 10/297,714. In one embodiment, the implantable device 4206 is configured to include at least a portion of the cord 4006. In one embodiment, the cord 4006 can be used to actuate, adjust, or position one or more sections of the implantable device 4206 as previously described in the aforementioned U.S. patent application. In one embodiment, the implantable device 4206 is coupled to the locking device 4000 at one end (e.g., the distal end). The cord 4006 is attached to and extended from the implantable device 4206 (and can be part of the implantable device 4206) through the locking device 4000. Locking the cord 4006 into position enables the moving sections of the implantable device 4206 that is controlled by the cord 4006 to be locked into position after proper positioning or adjustment.

It is to be understood that the locking device 4000 can be attached to other devices or medical devices that use a cord for adjustment. The locking device 4000 can be made an integral part of the device or be attached to an end of the device where the cord from that device extends in order to adjust and/or lock the cord. A cutting mechanism (not shown) can also be coupled to the locking device 4000 or delivery device 4050 to cut the extra length of the cord after deployment is complete.

Figure 21:
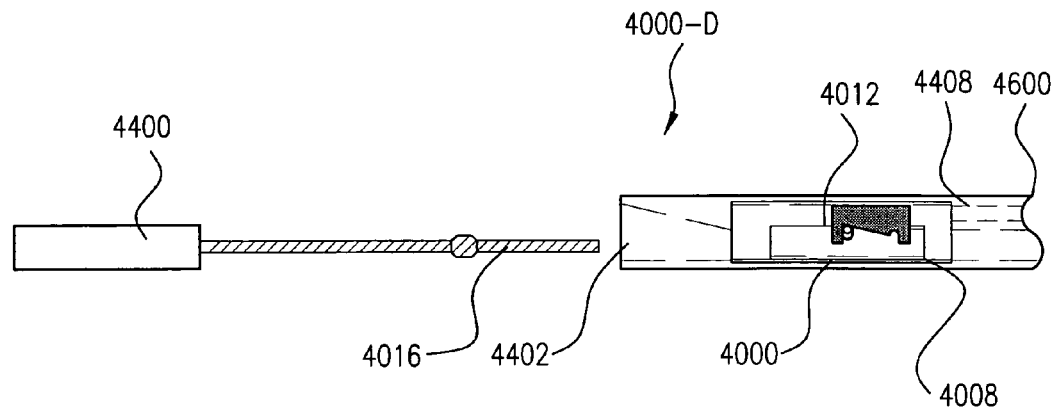
FIGS. 21-24 illustrate an exemplary embodiment of using a locking device to retrieve or reposition a device.
Figure 22:
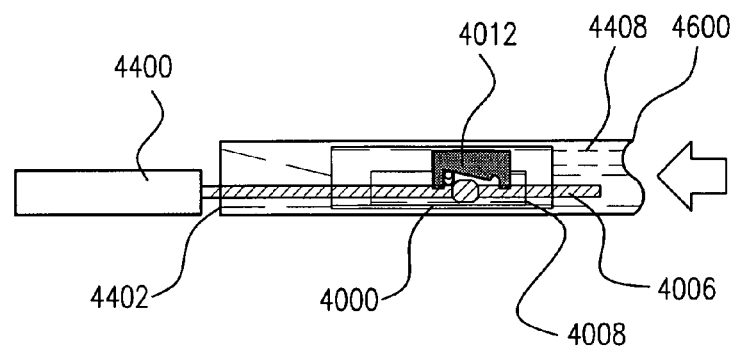
Figure 23:
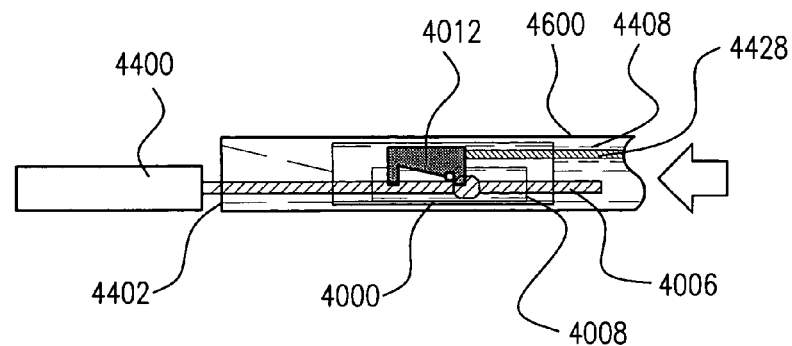

FIGS. 21-23 illustrate exemplary embodiments of using the locking device 4000 to retrieve a device 4400 that couples to or includes a cord 4006. In one embodiment, the locking device 4000 is disposed within a catheter 4600. In FIG. 21, the device 4400 is shown to couple to or include the cord 4006. The device 4400 can be a medical device or an implantable device that needs to be retrieved or repositioned. In this embodiment, the locking device 4000 does not need to include the cord 4006. The locking device 4000 can have any of the configurations described above. In addition, the locking device 4000 includes an actuator lumen 4408 in the outer housing 4002 and/or in a catheter attached to the locking device 4000 for an actuator 4228 to be inserted therethrough. The actuator 4228 can have any of the configurations of the actuators previously described, for example, a wire or a rod. Further, the locking device 4000 includes a guiding portion 4402 to guide the cord 4006 into the locking device 4000. In one embodiment, the guiding portion 4402 includes a funnel section placed at the distal end 4000-D of the locking device 4000. The funnel configuration facilitates the guiding of the cord 4006 into the inner housing 4008 of the locking device 4000.

FIG. 21 illustrates the device 4400 having the cord 4006 to be guided into the locking device 4000. FIG. 22 illustrates the locking device 4000 being advanced toward the device 4400 and the cord 4006 being guided into the inner housing 4008. The catheter 4600 can be configured to be a retrieval catheter that includes the locking device 4000 to facilitate the delivery of the locking device 4000 to the retrieval site. The retrieval catheter 4600 can be a delivery catheter wherein its distal end can include the locking device 4000. FIG. 23 shows that once the cord 4006 is guided into the inner housing 4008 of the locking member 4000, the actuator 4428 is advanced into the lumen 4408 to move the locking member 4012. The locking member 4012 locks the cord 4006 in place as previously described. In one embodiment, once the device 4400 is locked in placed so that it attaches to the locking device 4000, the device 4400 can be retrieved or repositioned as necessary. In one embodiment, the device 4400 is desired to be repositioned. In this embodiment, the actuator 4428 can be permanently attached to the locking member 4012 or some other push/pull mechanism as previously described.

Figure 24:
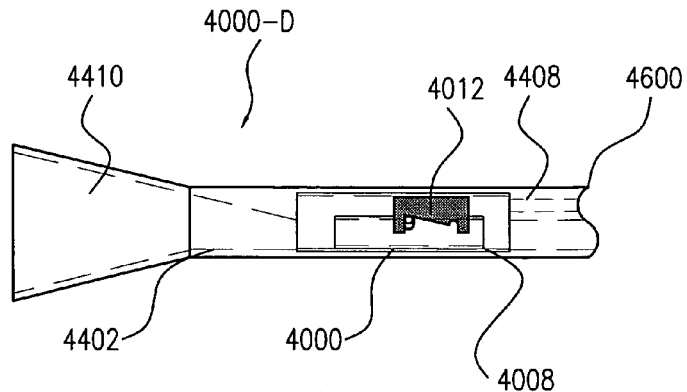

In another embodiment, the guiding portion 4402 of the locking device 4000 includes an additional guiding extension 4410 to improve the ease of capturing the cord 4006 in applications where an increase in the retrieving catheter's OD can be tolerated (FIG. 24). The guiding extension 4400 can have a more funnel shaped configuration as illustrated in FIG. 24. In one embodiment, the guiding extension 4400 has a resilient/elastic characteristic, such that it may be folded to enter the ID of other devices or catheters, such as a guide catheter, and then return to its shape (e.g., funnel shape) in a less constrained environment in which it is to be used.

Figure 25:
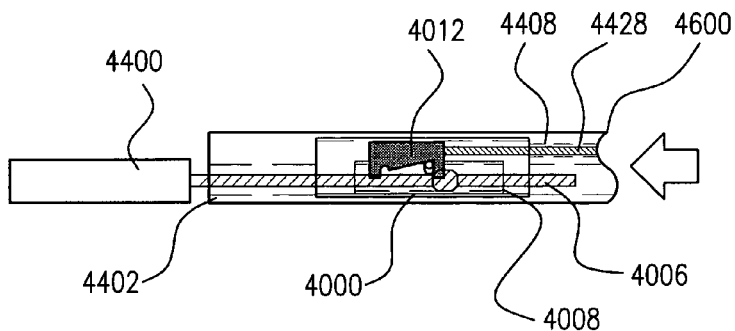
FIGS. 25-26 illustrate an exemplary embodiment of using a locking device to release a device.
Figure 26:
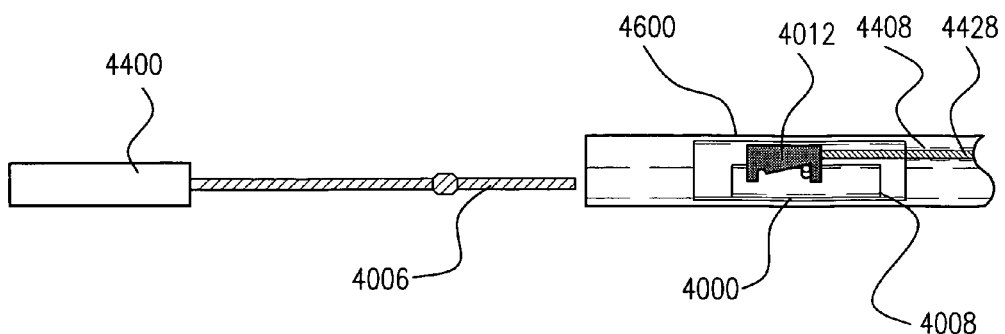

In another embodiment, the locking device 4000 is used in an application where it releases the device 4400 after the device 4400 has been positioned as desired. In one embodiment, the device 4400 is provided in a locked condition wherein the cord 4006 needs to be released after the device 4400 is deployed or positioned as desired. For instance, the cord 4006 can be the cord provided in the device 4400 which can be an annuloplasty delivery system as described in the aforementioned U.S. patent application. The cord 4006 could be adjusted (to cinch/adjust the telescope length) using the locking device. When the adjustment is complete (e.g., when mitral regurgitation is reduced acceptably), the locking device 4000 is unlocked and the annuloplasty device is left behind in the patient, e.g., in the coronary sinus. FIG. 25 illustrates the device 4400 being attached to the locking device 4000. FIG. 25 also illustrates that the actuator 4428 is inserted into the locking device 4000 to unlock the cord 4006. FIG. 26 illustrates that the locking device 4000 is removed after the positioning and adjustment of the device 4400 is completed and the device 4400 is left behind.

An exemplary method of using the embodiments of the locking device of the described herein in a patient, (e.g., in the vasculature or blood vessel of the patient), includes attaching or integrating the locking device to a medical device or implantable device. Attaching the distal portion of the cord of the locking device to a portion of the implantable device. The cord can also be the cord of the medical device as previously described U.S. patent application Ser. No. 10/297,714. The cord is also used to modulate the implantable device, for example, as the cord is used to telescope the telescoping members of the mentioned patent application. The medical device having the locking device attached or integrated thereto is inserted into the body of a patient. In one embodiment, a guide catheter is used to facilitate the insertion of the medical device having the locking device attached or integrated thereto. In one embodiment, a guidewire is first inserted into the patient to the treatment site (e.g., a blood vessel). In one embodiment, the treatment site is the coronary sinus of the heart. A guide catheter is advanced into the patient and to the treatment site over the guidewire. In one embodiment, the treatment site is the coronary sinus of the heart and in that embodiment, the guidewire is inserted into the heart and to the coronary sinus. Once the guide catheter is in place, the guidewire is withdrawn and the medical device having the locking device attached or integrated thereto is advanced to the treatment site through the guide catheter. Once the positioning of the medical device and the deployment of components of the medical device are achieved, for example, positioning an annuloplasty device and deploying anchoring members to reshape the blood vessel as previously described in the mentioned patent application, the actuator of the locking device is advanced to the locking device to lock the cord in place as previously described. Locking the cord in place locks the components of the medical device that need to be locked in place for proper functioning of the medical device. For instance, the anchor members of the annuloplasty device need to be locked in place to allow for the reshaping of the blood vessel as previously described in the mentioned application. In another instance, the locking device locks a cinching component deployed within the coronary sinus of the patient. In yet another instance, the locking device locks a telescoping member and the anchoring members in place within the coronary sinus. In the embodiments where the locking device is an integral part of the medical device, the locking device is left behind with the medical device. In the embodiments where the locking device is only attached to the medical device, the locking device can be removed after the positioning of the medical device is achieved.

It is to be understood that even though numerous characteristics and advantages of various embodiments have been set forth in the foregoing description together with details of structures and function of the various embodiments, this disclosure is illustrative only. Changes may be made in detail, especially matters of structure and management of parts, without departing from the scope of the various embodiments.

We claim:

1. A locking device comprising:
   an outer housing having a first lumen extending longitudinally therethrough, wherein the outer housing has a size that is suitable for advancement through a blood vessel;
   a cord disposed within the first lumen, the cord being freely moveable through the first lumen;
   a locking mechanism disposed within the first lumen and over the cord, the locking mechanism including an inner housing having a second lumen and an opening that exposes a portion of the cord; and a locking member, wherein the locking member has an upper surface and a lower surface, both of which curve towards an inner surface of the outer housing, the locking member has two longitudinal sides with each side having an incline extending from a detent upwards to reach an upper limit, wherein the incline faces the cord and is moveable longitudinally relative to the outer housing over the cord to lock or unlock the cord relative to the outer housing;
   an actuator configured to move the locking mechanism to lock or unlock the cord relative to the outer housing and a locking pin disposed over the opening.

2. The locking device of claim 1 wherein the opening cuts through a lateral axis of the inner housing.

3. The locking device of claim 2 wherein the actuator is configured to engage or disengage the locking member to move the locking member over the cord to lock or unlock the cord relative to the outer housing.

4. The locking device of claim 3 wherein the locking member further comprises an actuator engagement member configured to engage or disengage with the actuator.

5. The locking device of claim 3 wherein the locking member further comprises an actuator engagement member configured to engage the actuator, the actuator engagement member further comprising a loophole wherethrough a thread is disposed, pushing on the actuator advances the locking member in a direction of the actuator and pulling on the thread retracts the locking member in a direction of the pulling.

6. The locking device of claim 1 wherein the cord is configured with one or more interferences, the one or more interferences to cooperate with the locking mechanism to lock the cord relative to the outer housing.

7. The locking device of claim 1, with the proviso that the locking device does not have a biasing spring.

8. A locking device comprising:
   an outer housing having a first lumen, wherein the outer housing has a size that is suitable for advancement through a blood vessel;
   a cord disposed within the first lumen, the cord being moveable through the first lumen;
   a locking mechanism disposed within the first lumen and over the cord, the locking mechanism configured to lock or unlock the cord relative to the outer housing, wherein the locking mechanism comprises:
   an inner housing having a second lumen;
   the cord being disposed within the second lumen;
   the inner housing having an opening cutting through a lateral axis of the inner housing, the opening exposes a portion of the cord; and
   a locking member disposed on an outer surface of the inner housing, wherein the locking member has an upper surface and a lower surface, both of which curve towards an inner surface of the outer housing, the locking member has two longitudinal sides with each side having an incline extending from a detent upwards to reach an upper limit, wherein the incline faces the cord and is moveable longitudinally relative to the outer housing over the cord to lock or unlock the cord through the opening;
   an actuator configured to move the locking mechanism to lock or unlock the cord relative to the outer housing;
   a locking pin disposed over the opening; and
   the detent included within the locking member wherein the detent is engageable with the locking pin and wherein the locking pin is configured to allow the locking member to glide across the outer surface of the inner housing without disengaging the inner housing.

9. The locking device of claim 8 wherein the locking pin is configured to sit in the opening without being lodged into the second lumen.

10. The locking device of claim 8 wherein the detent is included at a lower region of the incline, the locking pin engages the detent to lock the cord in position relative to the outer housing.

11. The locking device of claim 8 wherein the cord is configured with one or more interferences, the one or more interferences to cooperate with the locking pin through the opening to lock the cord relative to the outer housing, when the locking pin engages the detent, the locking pin to press down onto the cord and one of the interferences to lock.

12. The locking device of claim 8, wherein the outer housing has a size that is suitable for advancement through a blood vessel of a patient.

13. A locking device comprising:
   an outer housing having a first lumen;
   an inner housing having a second lumen, the inner housing disposed within the first lumen and attached to the outer housing on one side;
   a cord disposed through the second lumen;
   an opening across a section of the inner housing, the opening being perpendicular to a longitudinal axis of the inner housing;
   a pin disposed within the opening, the pin and the opening being configured to prevent the pin from lodging onto the second lumen; and
   a locking member disposed on an outer surface of the inner housing and within the first lumen, the locking member has an upper surface and a lower surface, both of which curve towards an inner surface of the outer housing, the locking member has two longitudinal sides with each side having an incline extending from a detent upwards to reach an upper limit, wherein the incline faces the cord and is moveable longitudinally relative to the outer housing over the cord and the pin to engage with the pin and to cause the pin to lock or unlock the cord, wherein the pin is operable to slide along the incline.

14. The locking device of claim 13 wherein the inner housing has one side of the outer surface attached to one side of the inner surface of the outer housing.

15. The locking device of claim 13 further comprising:
an actuator capable of engaging the locking member to move the locking member to engage or disengage the pin to lock or unlock the cord.

16. The locking device of claim 13 further comprising:
an actuator engagement member coupling to the locking member to allow an actuator to engage or disengage the locking member.

17. The locking device of claim 13 further comprising:
an actuator engagement member coupling to the locking member to allow an actuator to engage the locking member, the actuator engagement member further includes a loophole wherethrough a thread is disposed, wherein pushing on the actuator advances the locking member in a direction of the actuator and pulling on the thread retracts the locking member in a direction of the pulling.

18. The locking device of claim 13 wherein the locking member includes the detent positioned at a lower point of the incline, the pin to engage the detent to lock the cord in position relative to the outer housing and the pin to disengage the detent to release the cord.

19. The locking device of claim 13 wherein the cord is configured with one or more interferences, the one or more interferences to cooperate with the locking member to lock the cord in position relative to the outer housing.

20. The locking device of claim 13 wherein the cord includes a deformable layer to facilitate locking of the cord in position relative to the outer housing.

21. The locking device of claim 13, wherein the locking device has a size that is suitable for advancement through a blood vessel of a patient.

22. The locking device of claim 13, with the proviso that the locking device does not have a biasing spring.

23. A medical device comprising:
an implantable medical device that is implantable within a patient coupling to a cord; and
a locking device that is capable of being introduced into the patient and configured to lock or unlock the cord, the locking device comprising; an outer housing having a first lumen extending longitudinally therethrough, the cord is disposed within the first lumen and freely moveable through the first lumen and an opening the exposes a portion of the cord; a locking mechanism disposed within the first lumen and over the cord, the locking mechanism including an inner housing having a second lumen; and a locking member that has an upper surface and a lower surface, both of which curve towards an inner surface of the outer housing, the locking member has two longitudinal sides with each side having an incline extending from a detent upwards to reach an upper limit, wherein the incline faces the cord and is moveable longitudinally relative to the outer housing over the cord to lock or unlock the cord relative to the outer housing; an actuator is used to move the locking mechanism in order to lock or unlock the cord relative to the locking device and a locking pin disposed over the opening.

24. The medical device of claim 23 wherein
the opening cuts through a longitudinal axis of the inner housing.

25. The medical device of claim 24 wherein the actuator is configured to engage or disengage the locking member to move the locking member over the cord to lock or unlock the cord relative to the outer housing.

26. The medical device of claim 25 wherein the locking member further comprises an actuator engagement member configured to engage or disengage with the actuator.

27. The medial device of claim 25 wherein the locking member further comprises an actuator engagement member configured to engage the actuator, the actuator engagement member further comprising a hole wherethrough a thread is disposed, pushing on the actuator advances the locking member in a direction of the actuator and pulling on the thread retracts the locking member in a direction of the pulling.

28. The medical device of claim 24
wherein the detent is engageable with the locking pin and wherein the locking pin is configured to allow the locking member to glide across the outer surface of the inner housing without disengaging the inner housing.

29. The medical device of claim 28 wherein the locking pin is configured to engage the opening without being dislodged into the second lumen.

30. The medical device of claim 28 wherein the detent is included at a lower region of the incline, the locking pin to engage the detent to lock the cord in position relative to the outer housing.

31. The medical device of claim 28 wherein the cord is configured with one or more interferences, the one or more interferences to cooperate with the locking mechanism to lock the cord relative to the outer housing.

32. The medical device of claim 31 wherein the cord is configured with one or more interferences, the one or more interferences to cooperate with the locking pin through the opening to lock the cord relative to the outer housing, when the locking pin engaging the detent, the locking pin pressing down onto the cord one of the interferences to lock.

33. The medical device of claim 23, wherein the locking device has a size that is suitable for advancement through a blood vessel of a patient.

34. The medical device of claim 23, with the proviso that the locking device does not have a biasing spring.

35. A medical device comprising:
a member actuated by a cord, the member being implantable within a patient; and
a locking device configured to lock or unlock the cord, the locking device comprising; an outer housing having a first lumen extending longitudinally therethrough, the cord is disposed within the first lumen and moveable through the first lumen a locking mechanism disposed within the first lumen and over the cord, the locking mechanism including an inner housing having a second lumen and an opening that exposes a portion of the cord; and a locking member that has an upper surface and a lower surface, both of which curve towards an inner surface of the outer housing, the locking member has two longitudinal sides with each side having an incline extending from a detent upwards to reach an upper limit, wherein the incline faces the cord and is moveable longitudinally relative to the outer housing over the cord to lock or unlock the cord relative to the outer housing a locking pin disposed over the opening; and an actuator to move the locking mechanism in order to lock or unlock the cord relative to the locking device.

36. The medical device of claim 35 wherein the locking device is coupled to the member at a proximal end of the member.

37. The medical device of claim 35 wherein the medical device and the locking device are configured to be deployed within a patient vasculature.

38. The medical device of claim 35, wherein the locking device has a size that is suitable for percutaneous advancement.

* * * * *